United States Patent
Fukazawa et al.

(10) Patent No.: US 9,322,788 B2
(45) Date of Patent: Apr. 26, 2016

(54) SURFACE INSPECTION APPARATUS, METHOD FOR INSPECTING SURFACE, EXPOSURE SYSTEM, AND METHOD FOR PRODUCING SEMICONDUCTOR DEVICE

(71) Applicant: Nikon Corporation, Tokyo (JP)

(72) Inventors: Kazuhiko Fukazawa, Kamakura (JP); Yoshihiko Fujimori, Yokohama (JP); Shinsuke Takeda, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/886,847

(22) Filed: Oct. 19, 2015

(65) Prior Publication Data

US 2016/0041108 A1 Feb. 11, 2016

Related U.S. Application Data

(62) Division of application No. 13/325,195, filed on Dec. 14, 2011.

(30) Foreign Application Priority Data

Dec. 14, 2010 (JP) ................. 2010-278308
Jan. 12, 2011 (JP) ................. 2011-004306

(51) Int. Cl.
| | |
|---|---|
| H01L 21/66 | (2006.01) |
| G01N 21/95 | (2006.01) |
| G01N 21/956 | (2006.01) |

(52) U.S. Cl.
CPC ...... *G01N 21/9501* (2013.01); *G01N 21/95607* (2013.01); *H01L 22/12* (2013.01); *G01N 2021/95615* (2013.01)

(58) Field of Classification Search
None
See application file for complete search history.

(56) References Cited

U.S. PATENT DOCUMENTS

| | | | |
|---|---|---|---|
| 6,313,913 | B1 | 11/2001 | Nakagawa et al. |
| 7,643,137 | B2 | 1/2010 | Sugihara et al. |
| 8,115,916 | B2 | 2/2012 | Hayano |
| 8,256,370 | B2 | 9/2012 | Kitano et al. |
| 8,422,009 | B2 | 4/2013 | Yamashita et al. |

(Continued)

FOREIGN PATENT DOCUMENTS

| | | |
|---|---|---|
| JP | H11-04076 | 2/1999 |
| JP | 2002-289503 | 10/2002 |

(Continued)

OTHER PUBLICATIONS

Notice of Reasons for Refusal issued in Japanese Patent Application No. 2012-548813, dated Aug. 18, 2015 (4 pages).

(Continued)

*Primary Examiner* — Angel Roman
(74) *Attorney, Agent, or Firm* — Finnegan, Henderson, Farabow, Garrett & Dunner, LLP

(57) ABSTRACT

A surface inspection apparatus includes: a detection unit configured to detect a first detection signal according to a first diffracted light beam and a second detection signal according to a second diffracted light beam; a storage unit which is configured to store a first reference data and a second reference data; and a determination unit which is configured to determine a processing condition of the pattern in the substrate as an inspection object substrate, based on consistency between the first detection signal and the first reference data, and consistency between the second detection signal and the second reference data.

9 Claims, 19 Drawing Sheets

(56) References Cited

U.S. PATENT DOCUMENTS

| | | |
|---|---|---|
| 2002/0100012 A1 | 7/2002 | Sutani et al. |
| 2004/0239918 A1 | 12/2004 | Sugihara et al. |
| 2006/0232769 A1 | 10/2006 | Sugihara et al. |
| 2008/0055575 A1 | 3/2008 | Nagasaka et al. |
| 2009/0123879 A1 | 5/2009 | Hidaka |
| 2009/0285991 A1 | 11/2009 | Kitano et al. |
| 2010/0271625 A1 | 10/2010 | Matsui |
| 2011/0026017 A1 | 2/2011 | Hayano |
| 2011/0235038 A1 | 9/2011 | Fukazawa et al. |
| 2015/0049314 A1 | 2/2015 | Fukazawa |

FOREIGN PATENT DOCUMENTS

| | | |
|---|---|---|
| JP | 2004-294194 A | 10/2004 |
| JP | 2006-80404 A | 3/2006 |
| JP | 2006-080404 A | 3/2006 |
| JP | 2006-105951 A | 4/2006 |
| JP | 2007-304054 | 11/2007 |
| JP | 2009-277870 A | 11/2009 |
| JP | 2010-153407 A | 7/2010 |
| JP | 2011-040434 A | 2/2011 |
| TW | 200823967 | 6/2008 |
| TW | 200929335 | 7/2009 |
| WO | WO 2009/091034 A1 | 7/2009 |
| WO | WO 2009-125805 A1 | 10/2009 |
| WO | WO 2010/052934 A1 | 5/2010 |
| WO | WO 2011-135867 A1 | 11/2011 |

OTHER PUBLICATIONS

International Search Report, from the Japanese Patent Office of corresponding PCT Application No. PCT/JP2011/078919, mailed Jan. 17, 2012.
First Office Letter of Chinese Patent Application No. 201180059328.5 dated Feb. 28, 2015, 6 pages.
Notice of Reasons for Refusal of Japanese Patent Application No. 2012-548796 dated Apr. 21, 2015, 4 pages.
International Preliminary Report on Patentability of International Application No. PCT/JP2011/078819 issued Jun. 18, 2013 (6 pages).
International Preliminary Report on Patentability of International Application No. PCT/JP2011/078919 issued Jun. 18, 2013 (6 pages).
Notice of Reasons for Refusal issued in Japanese Patent Application No. 2012-548796, dated Nov. 17, 2015 (4 pages).
Official Letter issued in counterpart Taiwanese Patent Application No. 100146165, dated Jan. 14, 2016 (15 pages).
Official Letter issued in related Taiwanese Patent Application No. 100146166, dated Jan. 11, 2016 (17 pages).

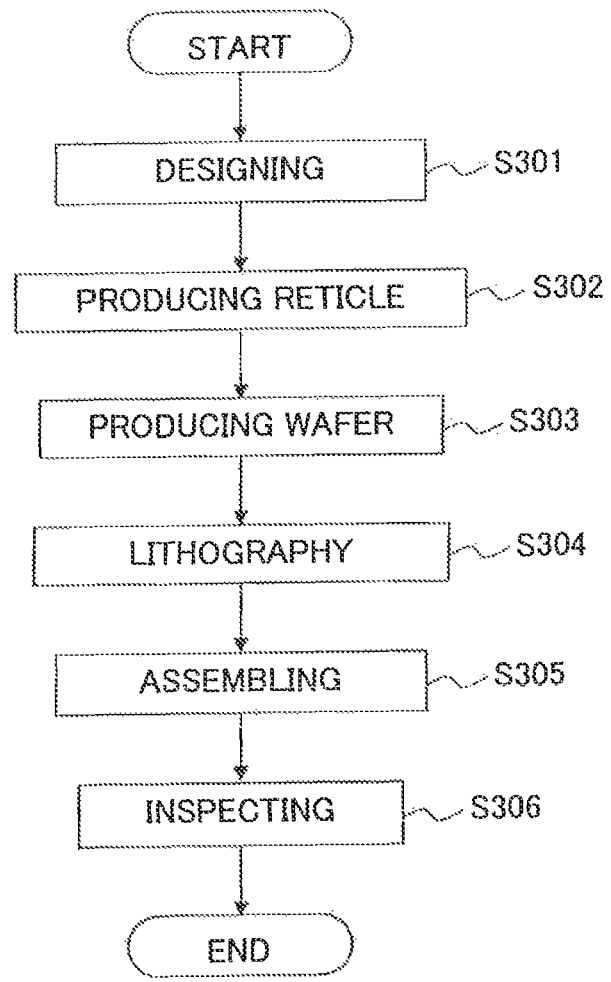

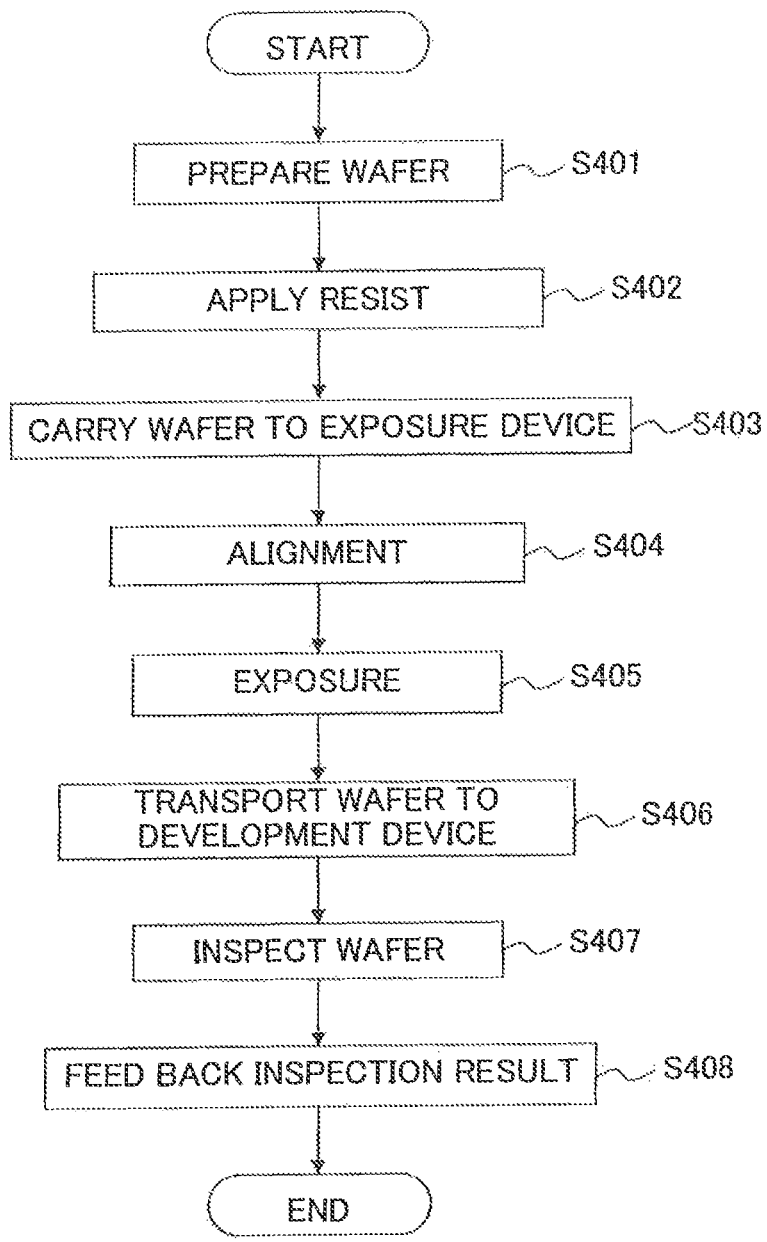

SURFACE INSPECTION APPARATUS, METHOD FOR INSPECTING SURFACE, EXPOSURE SYSTEM, AND METHOD FOR PRODUCING SEMICONDUCTOR DEVICE

CROSS REFERENCE TO RELATED APPLICATIONS

This is a division of Application Ser. No. 13/325,195, filed Dec. 14, 2011, which claims the right to priority based on Japanese patent Application No. 2010-278308, filed Dec. 14, 2010, and Japanese Patent Application No. 2011-004306, filed Jan. 12, 2011 in Japan, the entire content of all of which are incorporated herein by reference.

BACKGROUND

1. Field of the Invention

The present teaching relates to a surface inspection apparatus and a surface inspection method for inspecting substrate surfaces having a predetermined pattern. Further, the present teaching relates to an exposure system including such surface inspection apparatus and an exposure device, and a method for producing a semiconductor device utilizing such surface inspection method.

2. Description of the Related Art

Exposure devices of step-and-scan type carry out exposure on one shot for a semiconductor wafer by relatively moving a reticle stage (i.e. a mask substrate with a mask pattern formed therein) and a wafer stage (i.e. a wafer on which a semiconductor pattern is to be formed) to scan just one shot while irradiating with a slit-shaped Light beam via the mask pattern and a projection lens. In so doing, because the size of an exposure shot is determined by the relative distance of scanning between the long side or the slit (light) and the reticle stage, it is possible to enlarge the exposure shot.

For such kind of exposure devices, a focus control (a control of the focusing state of the pattern on the wafer surface) is important. Therefore, the focusing state of the exposure device on the wafer surface is monitored (here, the focusing control is not limited to problems due to defocusing, but refers to the control of variation of the focusing state within a shot or on the entire wafer surface). In order to measure the focusing state of the exposure device, for example, there are methods predetermined as utilize a dedicated mask substrate to expose and develop a test pattern, and measure a focus offset from positional deviation of the obtained test pattern (for example, see Japanese Patent Application Laid-Open No. 2002-289503).

SUMMARY

According to an aspect of the present teaching, there is provided a surface inspection apparatus which inspects a surface of a substrate having a pattern formed thereon and processed under a predetermined processing condition, including:

a detection unit which is configured to illuminate, with an illumination light beam, a predetermined region of the surface of the substrate to detect a first detection signal according to a first diffracted light beam propagating in a first direction from the pattern within the predetermined region and a second detection signal according to a second diffracted light beam propagating in a second direction different from the first direction;

a storage unit which is connected to the detection unit and which is configured to store a first reference data and a second reference data with respect to at least one substrate having a plurality of patterns processed under a plurality of predetermined processing conditions, the first reference data indicating a relationship between the first detection signal detected by the detection unit and the plurality of predetermined processing conditions and the second reference data denoting a relationship between the second detection signal detected by the detection unit and the plurality of predetermined processing conditions; and a determination unit which is connected to the detection unit and which is configured to determine a processing condition of the pattern in the substrate as an inspection object substrate, based on consistency between the first detection signal for the inspection object substrate detected by the detection unit and the first reference data, and consistency between the second detection signal for the inspection object substrate detected by the detection section and the second reference data.

BRIEF DESCRIPTION OF THE DRAWINGS

FIG. 19 is a flowchart showing a semiconductor device fabrication method; and FIG. 20 is a flowchart showing a lithography process.

DESCRIPTION OF THE EMBODIMENT

Figure 1:
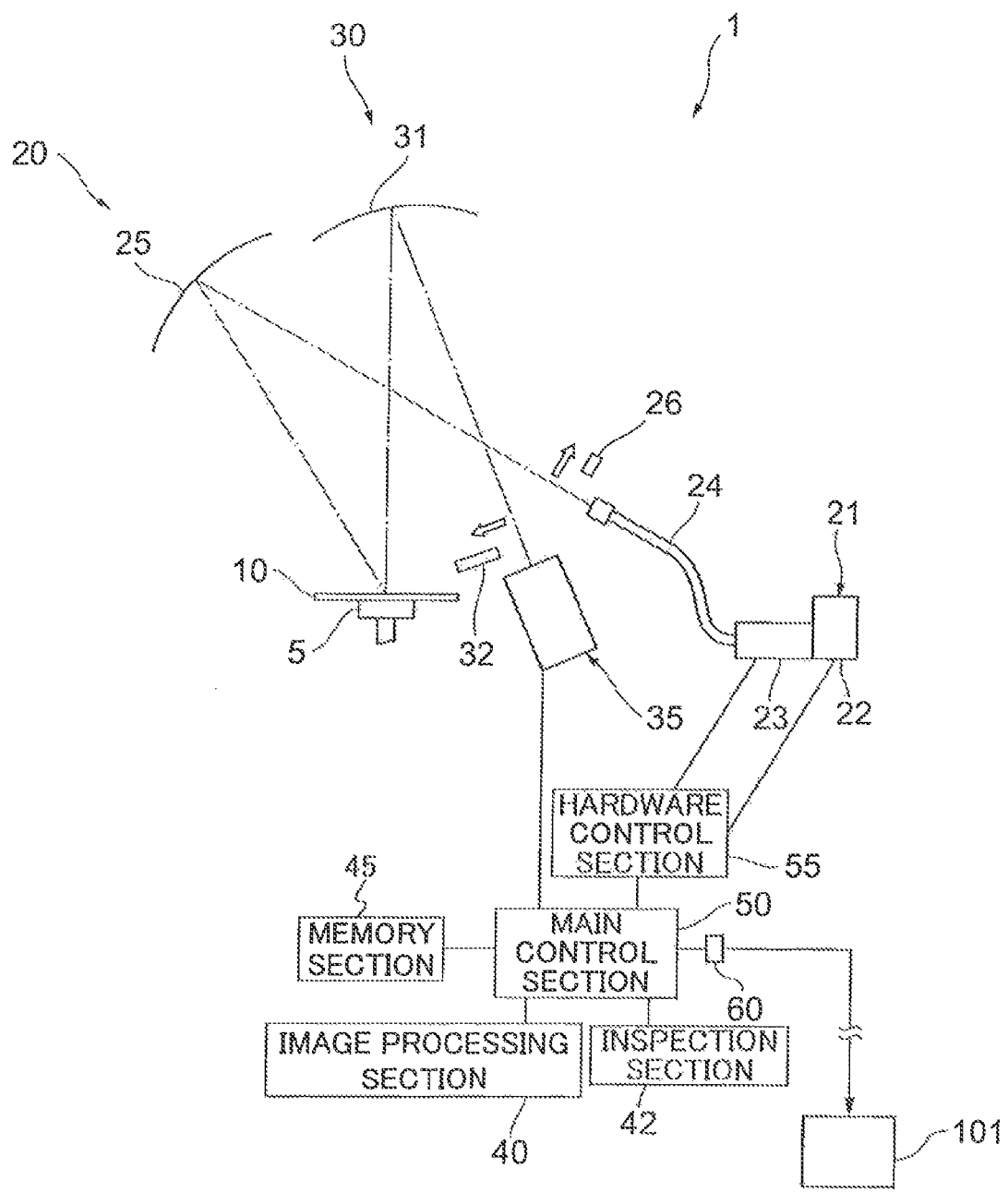
FIG. 1 is a schematic configuration diagram of a surface inspection apparatus.

Hereinbelow, referring to the accompanying drawings, an embodiment of the present teaching will be explained. FIG. 1 shows a surface inspection apparatus of the embodiment, which is utilized to inspect the surface of a semiconductor substrate wafer 10 (to be referred to as a wafer 10 hereinbelow). As shown in FIG. 1, the surface inspection apparatus 1 of the embodiment includes a stage 5 configured to support the approximately disk-shaped wafer 10, which is carried therein by a carrier device (not shown) and placed on the stage 5 while being fixed and held by vacuum suction. The stage 5 supports the wafer 10 to be rotatable (within the surface of the wafer 10) with a rotational symmetrical axis of the wafer 10 (the central axis of the stage 5) as the rotation axis. For convenience, the direction of the wafer due to this rotation is to be referred to as the wafer azimuth angle. Further, the stage 5 can tilt the wafer 10 about an axis extending through the support plane of supporting the wafer 10 (a tilting axis), and can adjust the incidence angle of illumination light.

Further, the surface inspection apparatus 1 includes an illumination system 20 configured to irradiate the entire surface of the wafer 10 supported on the stage 5 with an illumination light beam as a parallel light beam, a light receiving system 30 configured to condense reflected light, diffracted light and the like from the entire surface of the wafer 10 receiving the irradiation of the illumination light beam, an imaging device 35 configured to take and detect an image of the surface of the wafer 10 receiving the light beam condensed by the light receiving system 30, an image processing section 40, an inspection section 42, and a storing section (a memory section) 45. The illumination system 20 includes an illumination unit 21 configured to emit the illumination light beam, and an illumination-side concave mirror 25 configured to reflect the illumination light beam emitted from the illumination unit 21 toward the surface of the wafer 10. The illumination unit 21 includes a light source 22 such as a metal halide lamp, a mercury lamp and the like, a light adjusting section (a dimmer) 23 configured to adjust light intensity by extracting the light beam having a predetermined wavelength from the light from the light source 22, and a light guiding fiber 24 configured to guide the light beam from the light adjusting section 23 as the illumination light beam to the illumination-side concave mirror 25. Further, the surface inspection apparatus 1 includes a main control section 50 and a hardware control section 55 connected to the main control section 50. The main control section 50 controls the light source 22 and the light adjusting section 23 via the hardware control section 55 and, furthermore, receives digital image data from the imaging device 35 and sends the same to the image processing section 40. The data processed in the image processing section 40 is then sent by the main control section 50 to the inspection section 42 to be inspected. The inspection result and the digital image data are sent by the main control section 50 to the storing section 45 to be stored.

Then, the light beam from the light source 22 is transmitted through the light adjusting section 23, and the illumination light beam of a predetermined intensity having a predetermined wavelength (248 nm, for example) is emitted from the light guiding fiber 24 toward the illumination-side concave mirror 25. Then, because the exit portion of the light guiding fiber 24 is arranged on the focal plane of the illumination-side concave mirror 25, the illumination light beam emitted from the light guiding fiber 24 to the illumination-side concave mirror 25 becomes a parallel light beam due to the illumination-side concave mirror 25 to irradiate the surface of the wafer 10 held on the stage 5. Further, it is possible to adjust the relation between the incoming angle and the outgoing angle to the wafer 10 for the illumination light by tilting the stage 5 around the tilting angle to change the angle of placing the wafer 10.

Figure 2:
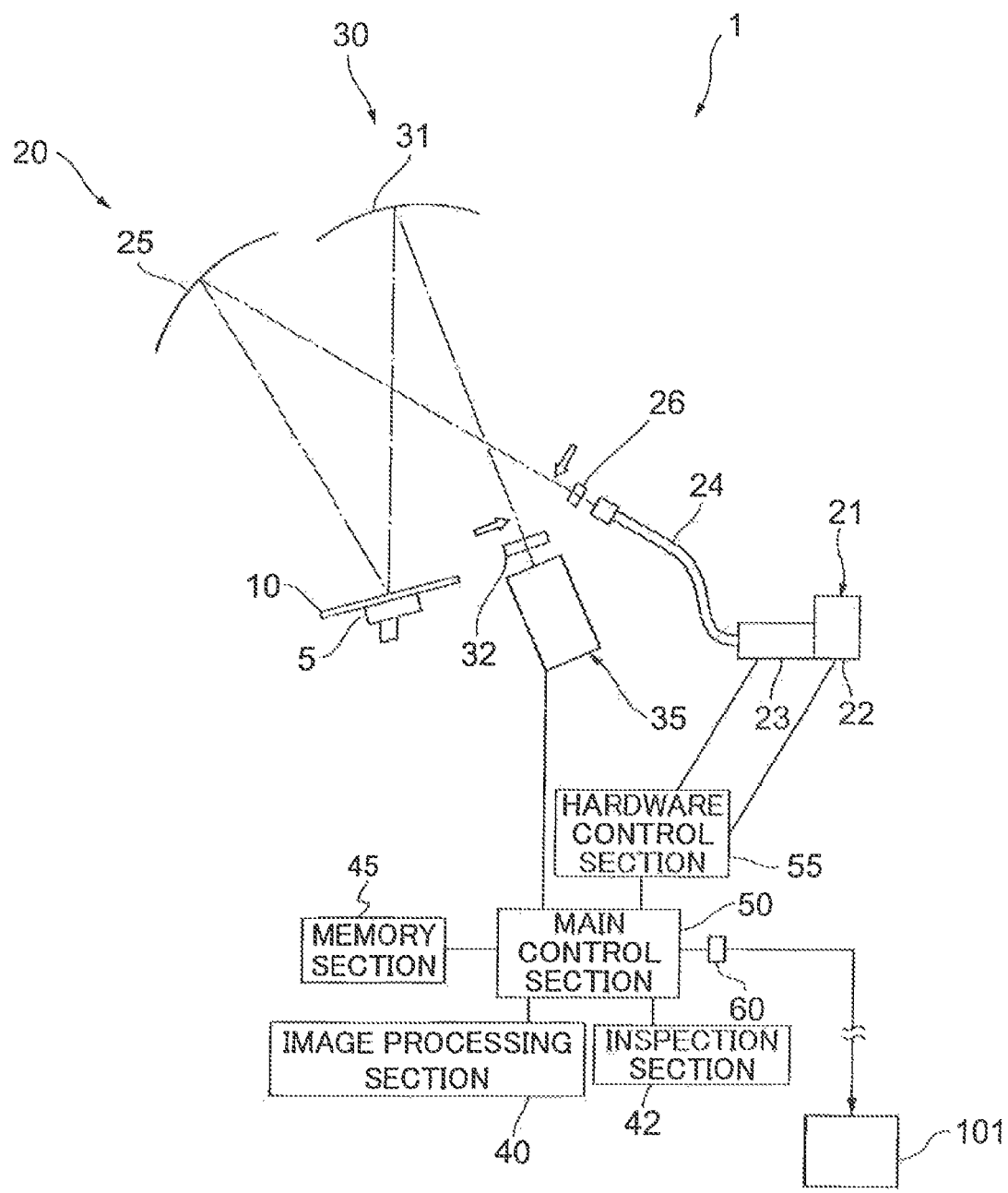
FIG. 2 shows a state of inserting a polarizing filter into an optical path of the surface inspection apparatus.

Further, between the light guiding fiber 24 and the illumination-side concave mirror 25, an illumination-side polarizing filter 26 is provided to be insertable into and removable from the optical path. As shown in FIG. 1, under a condition that the illumination-side polarizing filter 26 is removed from the optical path, inspection is carried out by utilizing diffracted light (to be referred to as diffraction inspection hereinbelow for convenience) and, as shown in FIG. 2, under a condition that the illumination-side polarizing filter 26 is inserted in the optical path, inspection is carried out by utilizing polarized light (by utilizing a change in polarization state due to form birefringence). This inspection will be referred to as PER inspection hereinbelow for convenience, and the illumination-side polarizing filter 26 will be described in detail hereinafter.

The light receiving system 30 condenses the exit light beam (diffracted or reflected light beam) from the surface of the wafer 10. The light receiving system 30 mainly includes a light-receiving-side concave mirror 31 provided to face the stage 5. The exit light beam condensed by the light-receiving-side concave mirror 31 (diffracted or reflected light beam) reaches the imaging plane of the imaging device 35 to form an image of the wafer 10.

Further, a light-receiving-side polarizing filter 32 is provided to be insertable into and removable from the optical path between the light-receiving-side concave mirror 31 and the imaging device 35. As shown in FIG. 1, under a condition that the light-receiving-side polarizing filter 32 is removed from the optical path, diffraction inspection is carried out and, as shown in FIG. 2, under a condition that the light-receiving-side polarizing filter 32 is inserted in the optical path, the PER inspection is carried out (the light-receiving-side polarizing filter 32 will be described in detail hereinafter).

The imaging device 35 photoelectrical converts the surface image of the wafer 10 formed on the imaging plane to generate an image signal (digital image data), and sends the signal to the main control section 50, which outputs the image signal to the image processing section 40. The image processing section 40 generates a digital image of the wafer 10 based on the image signal of the wafer 10 inputted from the imaging device 35. The storing section 45 previously stores image data of nondefective wafers. The inspection section 42 receives and compares the image data of the wafer 10 from the main control section 50 and the image data of nondefective wafers to inspect whether or not there is any defect (abnormity) in the surface of the wafer 10. Then, the inspection result from the inspection section 42 and the image of the relevant wafer 10 are outputted on an image display device (not shown). Further, the inspection section 42 is configured to be capable of finding a focusing state in exposure due to an exposure device 101 by utilizing the wafer image (details will be described hereinafter). Further, when easy to be affected by lower layers, it is possible to reduce influence from the lower layers influence by arranging the illumination-side polarizing filter 26 in the illumination system 20 such that the illumination light may become s-polarized light, and illuminating with the s-polarized light. Further, in this case, the light-receiving-side polarizing filter 32 should also be removed from the optical path.

Figure 3:
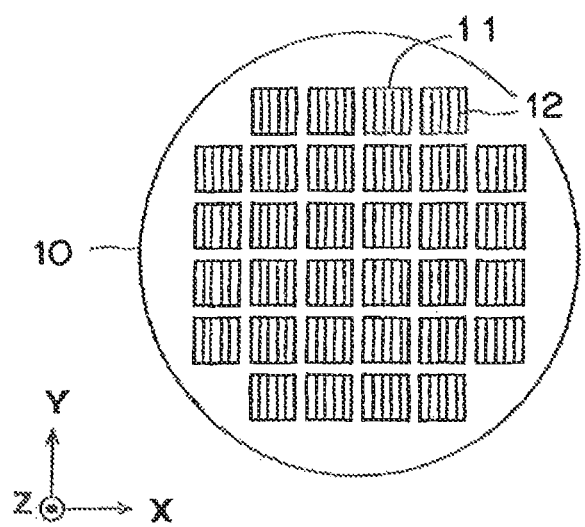
FIG. 3 is an external view of a surface of a semiconductor wafer.

However, the exposure device 101 projects a predetermined mask pattern on the wafer 10 and exposes the uppermost resist film of the wafer 10. The wafer 10 is developed by a development device (not shown) and then carried onto the stage 5 by a carrier device (not shown) from a wafer cassette (not shown) or the development device. Further, at this time, the wafer 10 is carried onto the stage 5 in a state of being aligned with the pattern or the outer edge (notch, orientation flat or the like) of the wafer 10 as the reference. Further, on the surface of the wafer 10, as shown in FIG. 3, a plurality of chip regions 11 are arranged horizontally and vertically (in X- and Y-directions in FIG. 3), and in each chip region 11, a repetitive pattern 12 is formed as a semiconductor pattern such as a line pattern, a hole pattern, or the like. Although a plurality of chip regions may often be included in one exposed shot, for the easiness to understand. FIG. 3 shows one chip as one shot. Further, while processing speed can be raised by illuminating and receiving light wholly and collectively, it is still possible to illuminate and receive light for one shot or an even smaller area as the object. Further, the exposure device 101 is an exposure device of the aforementioned step-and-scan type, is electrically connected to a signal output portion 60 of the surface inspection apparatus 1 of the embodiment via cables and the like, and is configured to be capable of exposure control adjustment based on the data (signal) from the surface inspection apparatus 1.

In order to utilize the surface inspection apparatus 1 configured in the above manner to carry out diffraction inspection of the surface of the wafer 10, first, the illumination-side polarizing filter 26 and the light-receiving-side polarizing filter 32 are removed from the optical path as shown in FIG. 1, and the wafer 10 is carried onto the stage 5 by the carrier device (not shown). Further, it is possible to place the wafer 10 on the stage 5 in predetermined position and direction since an alignment mechanism (not shown) acquires positional information of the pattern formed in the surface of the wafer 10 in carrying.

Next, the stage 5 is rotated such that the direction of illuminating the surface of the wafer 10 coincides with the repetitive direction of the pattern (in the case of a line pattern, the illumination direction is perpendicular to the line). Further, the stage 5 is positioned to satisfy the following equation (1) by Huygens' principle (to tilt the stage 5), where P represents the pattern pitch, λ represents the wavelength of the illumination light beam irradiating the surface of the wafer 10, θ1 represents the incidence angle of the illumination light beam, and θ2 represents the exit angle of the nth-order diffracted light beam.

$$P = n \times \lambda / \{\sin(\theta 1) - \sin(\theta 2)\} \quad \text{(Eq. 1)}$$

Next, the illumination system 20 irradiates the surface of the wafer 10 with the illumination light beam. When irradiating the surface of the wafer 10 with the illumination light beam under such a condition, the light beam from the light source 22 in the illumination unit 21 is transmitted through the light adjusting section 23. The illumination light beam of a predetermined intensity having a predetermined wavelength (248 nm, for example) exits from the light guiding fiber 24 to the illumination-side concave mirror 25, and the illumination light beam reflected by the illumination-side concave mirror 25 becomes a parallel light beam to irradiate the surface of the wafer 10. The diffracted light beam diffracted by the surface of the wafer 10 is condensed by the light-receiving-side concave mirror 31, and reaches the imaging plane of the imaging device 35 to form a (diffraction) image of the wafer 10. A diffraction condition is defined to be the condition of diffracted light determined by combining the wafer azimuth angle, illumination wavelength, illumination angle, exit angle, diffracted times, and the like.

Here, the imaging device 35 photoelectrical converts the surface image of the wafer 10 formed on the imaging plane to generate an image signal, and outputs the image signal to the image processing section 40. The image processing section 40 generates a digital image of the wafer 10 based on the image signal of the wafer 10 inputted from the imaging device 35 (the digital image of the wafer 10 based on diffracted light will be referred to as a diffraction image hereinbelow for convenience). Further, the image processing section 40 sends the diffraction image to the inspection section 42 via the main control section 50 after generating the diffraction image of the wafer 10, and the inspection section 42 compares the image data of the wafer 10 with the image data of nondefective wafers to inspect whether or not there is any defect (abnormity) in the surface of the wafer 10. Then, the inspection result from the image processing section 40 and inspection section 42 and the diffraction image of the relevant wafer 10 are outputted on the image display device (not shown).

Figure 4:
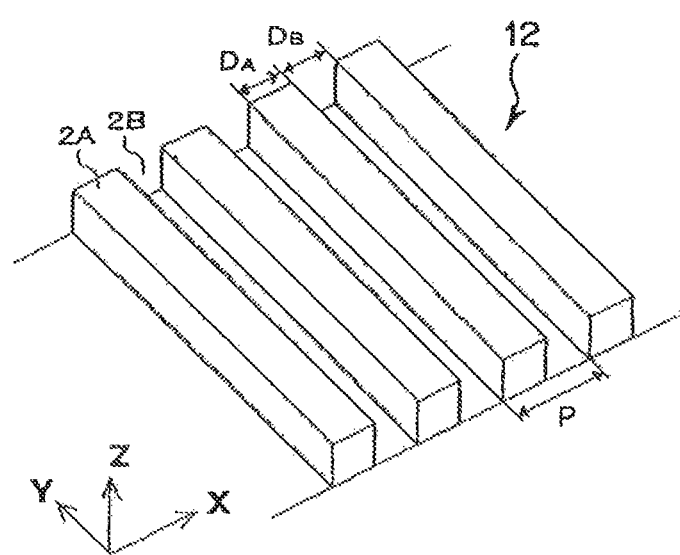
FIG. 4 is a perspective view for explaining a concavo-convex structure of a repetitive pattern.

Next, explanations will be made with respect to the case of carrying out the PER inspection of the surface of the wafer 10 by the surface inspection apparatus 1. Further, the repetitive pattern 12 is supposed to be, as shown in FIG. 4, a resist pattern (line pattern) where a plurality of line portions 2A are aligned with a certain pitch P along the latitudinal direction (X-direction). Further, there is a space portion 2B between adjacent line portions 2A. Further, the direction of aligning the line portions 2A (X-direction) will be referred to as the "repetitive direction of the repetitive pattern 12".

Here, the design value of line width $D_A$ of the line portions 2A in the repetitive pattern 12 is supposed to be ½ of the pitch P. When the repetitive pattern 12 is formed just as following the design value, then the line width $D_A$ of the line portions 2A is equal to the line width $D_B$ of the space portions 2B, and the volume ratio between the line portion 2A and the space portion 2B is approximately 1:1. On the other hand, when the exposure focus deviates from a correct value in forming the repetitive pattern 12, then the pitch P does not change but the line width $D_A$ of the line portions 2A differs from the design value and from the line width $D_B$ of the space portion 2B and, as a result, the volume ratio between the line portion 2A and the space portion 2B deviates from 1:1.

The PER inspection utilizes the change in the volume ratio between the line portion 2A and the space portion 2B in the repetitive pattern 12 as described above to carry out abnormity inspection of the repetitive pattern 12. Further, in order to simplify explanations, the ideal volume ratio (design value) is supposed to be 1:1. The change in volume ratio is because the exposure focus deviates from the correct value, and appears in each shot region of the wafer 10. Further, it is possible to rephrase the volume ratio as the area ratio of cross-section shape.

Figure 5:
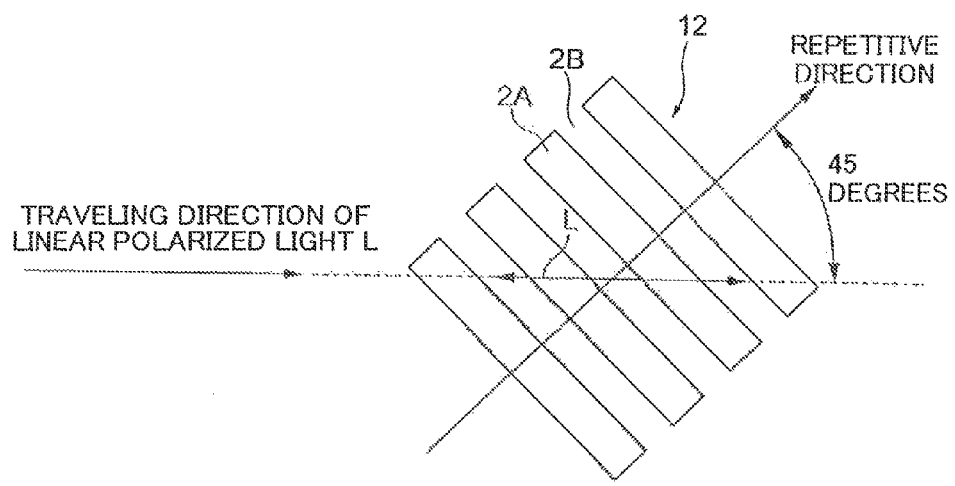
FIG. 5 is a diagram for explaining a state of inclination between the incidence surface of a linear polarized light and the repetitive direction of the repetitive pattern.

In the PER inspection, as shown in FIG. 2, the illumination-side polarizing filter 26 and the light-receiving-side polarizing filter 32 are inserted into the optical path. Further, when carrying out the PER inspection, the stage 5 tilts the wafer 10 at an inclination angle such that the light receiving system 30 can receive the specular light from the wafer 10 irradiated by the illumination light. Further, the stage 5 stops at a predetermined rotation position to maintain the repetitive direction of the repetitive pattern 12 in the wafer 10 as 45 degrees oblique to the oscillation direction of the illumination light (linear polarized light L) on the surface of the wafer 10 as shown in FIG. 5. According to the knowledge of the present inventors, when the angle between the repetitive direction of the repetitive pattern 12 in the wafer 10 and the oscillation direction of the illumination light is set to be about 45 degrees, it is possible to maximize the amount of light for inspecting the repetitive pattern 12. Further, according to the knowledge of the present inventors, when the angle between the repetitive direction of the repetitive pattern 12 in the wafer 10 and the oscillation direction of the illumination light is set to be about 22.5 degrees or about 67.5 degrees, it is possible to enhance the sensitivity of inspection. It goes without saying that the angle is not limited to these degrees but may be set in arbitrary angular directions.

The illumination-side polarizing filter 26 is provided between the light guiding fiber 24 and the illumination-side concave mirror 25, and its transmission axis is set in a predetermined azimuth direction to extract the linear polarized light from the light beam from the illumination unit 21 according to the transmission axis. At this time, because the exit portion of the light guiding fiber 24 is arranged in the focal position of the illumination-side concave mirror 25, the illumination-side concave mirror 25 makes the light transmitted through the illumination-side polarizing filter 26 be a parallel light beam to irradiate the substrate wafer 10. In this manner, the light beam exiting the light guiding fiber 24 becomes the linear polarized light L of p-polarization (see FIG. 5) via the illumination-side polarizing filter 26 and the illumination-side concave mirror 25 to irradiate the entire surface of the wafer 10 as an illumination light.

At this time, because the propagating direction of the linear polarized light L (the direction of the main light beam of the linear polarized light L reaching any points on the surface of the wafer 10) is approximately parallel to the optical axis, the incidence angle of the linear polarized light L at each point of the wafer 10 is identical to each other due to the parallelity. Further, because the linear polarized light L incident on the wafer 10 is p-polarized, as shown in FIG. 5, when the repetitive direction of the repetitive pattern 12 is set at a 45-degree angle to the incidence surface of the linear polarized light L (the propagating direction of the linear polarized light L on the surface of the wafer 10), the angle formed between the oscillation direction of the linear polarized light L on the surface of the wafer 10 and the repetitive direction of the repetitive pattern 12 is also set at 45 degrees. In other words, the linear polarized light L enters the repetitive pattern 12 such that the oscillation direction of the linear polarized light L on the surface of the wafer 10 is inclined 45 degrees with respect to the repetitive direction of the repetitive pattern 12 and that the linear polarized light L obliquely traverses the repetitive pattern 12.

The specular light beam reflected by the surface of the wafer 10 is condensed by the light-receiving-side concave mirror 31 of the light receiving system 30 and reaches the imaging plane of the imaging device 35. At this time, the polarization state of the linear polarized light L changes due to the form birefringence in the repetitive pattern 12. The light-receiving-side polarizing filter 32 is provided between the light-receiving-side concave mirror 31 and the imaging device 35, and the azimuth of the transmission axis of the light-receiving-side polarizing filter 32 is set to be perpendicular to the transmission axis of the illumination-side polarizing filter 26 described above (a crossed Nichol state). Therefore, the light-receiving-side polarizing filter 32 can transmit the polarized component (the s-polarized component, for example) almost orthogonal in oscillation direction to the linear polarized light L in the specular light from the wafer 10 (the repetitive pattern 12) to lead the same to the imaging device 35. As a result, on the imaging plane of the imaging device 35, a reflection image of the wafer 10 is formed by the polarized component almost orthogonal in oscillation direction to the linear polarized light L among the specular light beams from the wafer 10. Further, it is possible to improve the sensitivity by making the light-receiving-side polarizing filter 32 be rotatable about the optical axis and adjust the same such that the minor axis of the elliptically polarized specular light coincides with the transmission axis of the light-receiving-side polarizing filter 32. In this case, the adjusting angle is a few degrees. Therefore, it is possible to say that the azimuth of the transmission axis of the light-receiving-side polarizing filter 32 is set to be substantially perpendicular to the transmission axis of the illumination-side polarizing filter 26.

In order for the surface inspection apparatus 1 to carry out the PER inspection of the surface of the wafer 10, first, as shown in FIG. 2, the illumination-side polarizing filter 26 and the light-receiving-side polarizing filter 32 are inserted into the optical path, and the wafer 10 is carried onto the stage 5 by the carrier device (not shown). Further, it is possible to place the wafer 10 on the stage 5 in predetermined position and direction since the alignment mechanism (not shown) acquires positional information of the pattern formed in the surface of the wafer 10 in carrying. Further, at this time, the stage 5 tilts the wafer 10 at an inclination angle such that the light receiving system 30 can receive the specular light from the wafer 10 irradiated by the illumination light. Further, the stage 5 stops at a predetermined rotation position to maintain the repetitive direction of the repetitive pattern 12 in the wafer 10 as 45 degrees oblique to the oscillation direction of the illumination light (linear polarized light L) on the surface of the wafer 10.

Next, the illumination system 20 irradiates the surface of the wafer 10 with the illumination light beam. When irradiating the surface of the wafer 10 with the illumination light beam under such a condition, the light beam exiting from the light guiding fiber 24 of the illumination unit 21 becomes the linear polarized light L of P-polarization via the illumination-side polarizing filter 26 and the illumination-side concave mirror 25 to irradiate the entire surface of the wafer 10 as an illumination light. The specular light beam reflected by the surface of the wafer 10 is condensed by the light-receiving-side concave mirror 31, and reaches the imaging plane of the imaging device 35 to form a (reflection) image of the wafer 10.

At this time, the polarization state of the linear polarized light L changes due to the form birefringence in the repetitive pattern 12. The light-receiving-side polarizing filter 32 can transmit the polarized component almost orthogonal in oscillation direction to the linear polarized light L in the specular light from the wafer 10 (the repetitive pattern 12), i.e., extract the change in the polarization state of the linear polarized light L, to lead the same to the imaging device 35. As a result, a reflection image of the wafer 10 is formed on the imaging plane of the imaging device 35, by the polarized component almost orthogonal in oscillation direction to the linear polarized light L among the specular light beams from the wafer 10.

Here, the imaging device 35 photoelectrical converts the surface image (reflection image) of the wafer 10 formed on the imaging plane to generate an image signal (digital image data), and outputs the image signal to the image processing section 40 via the main control section 50. The image processing section 40 generates a digital image of the wafer 10 based on the image signal of the wafer 10 inputted from the imaging device 35 (the digital image of the wafer 10 based on polarized light beam will be referred to as the polarization image hereinbelow for convenience). Further, the image processing section 40 sends the polarization image to the inspection section 42 via the main control section 50 after generating the polarization image of the wafer 10, and the inspection section 42 compares the image data of the wafer 10 with the image data of nondefective wafers to inspect whether or not there is any defect (abnormity) in the surface of the wafer 10. Further, since the signal intensity (brightness value) of the reflection image of nondefective wafers is conceivably to show the maximum signal intensity (brightness value), for example, "abnormity" is determined when the change in signal intensity (brightness) compared with nondefective wafers is greater than a predetermined threshold value (allowable value), while "normality" is determined when it is less than the threshold value. Then, the inspection result from the image processing section 40 and the inspection section 42, and the polarization image of the relevant wafer 10 are outputted on the image display device (not shown).

Further, the signal intensity refers to that according to the light detected by the imaging element of the imaging device 35 such as diffraction efficiency, intensity ratio, energy ratio, and the like. The present teaching is not limited to the above diffraction inspection and PER inspection, it is also possible to carry out inspection based on the specular light from the surface of the wafer 10 (to be referred to as the specular inspection hereinbelow for convenience). When carrying out the specular inspection, the image processing section 40 generates a digital image based on the specular light from the surface of the wafer 10 (to be referred to as the specular image hereinbelow for convenience) to inspect whether or not there is any defect (abnormity) in the surface of the wafer 10 based on the generated specular image of the wafer 10.

Further, the inspection section 42 can find a focus curve clue to the diffracted light of the exposure device 101 (a curve showing a relationship between the focus offset and the signal intensity) by utilizing an image of a developed wafer exposed under the condition of changing the focus offset of the exposure device 101 for each shot. Utilizing this focus curve to find the focus offset for the signal intensity of diffracted light to become maximum for each minute region in one shot, it is possible to find inclination of the image plane of the mask pattern projected and exposed by the exposure device 101. According to the knowledge of the present inventors, in the case of diffracted light, when the line-and-space duty ratio is set to be not less than ten (one line unit to ten or more space units), then the focus offset in which the signal intensity becomes maximum is the best focus.

Figure 6:
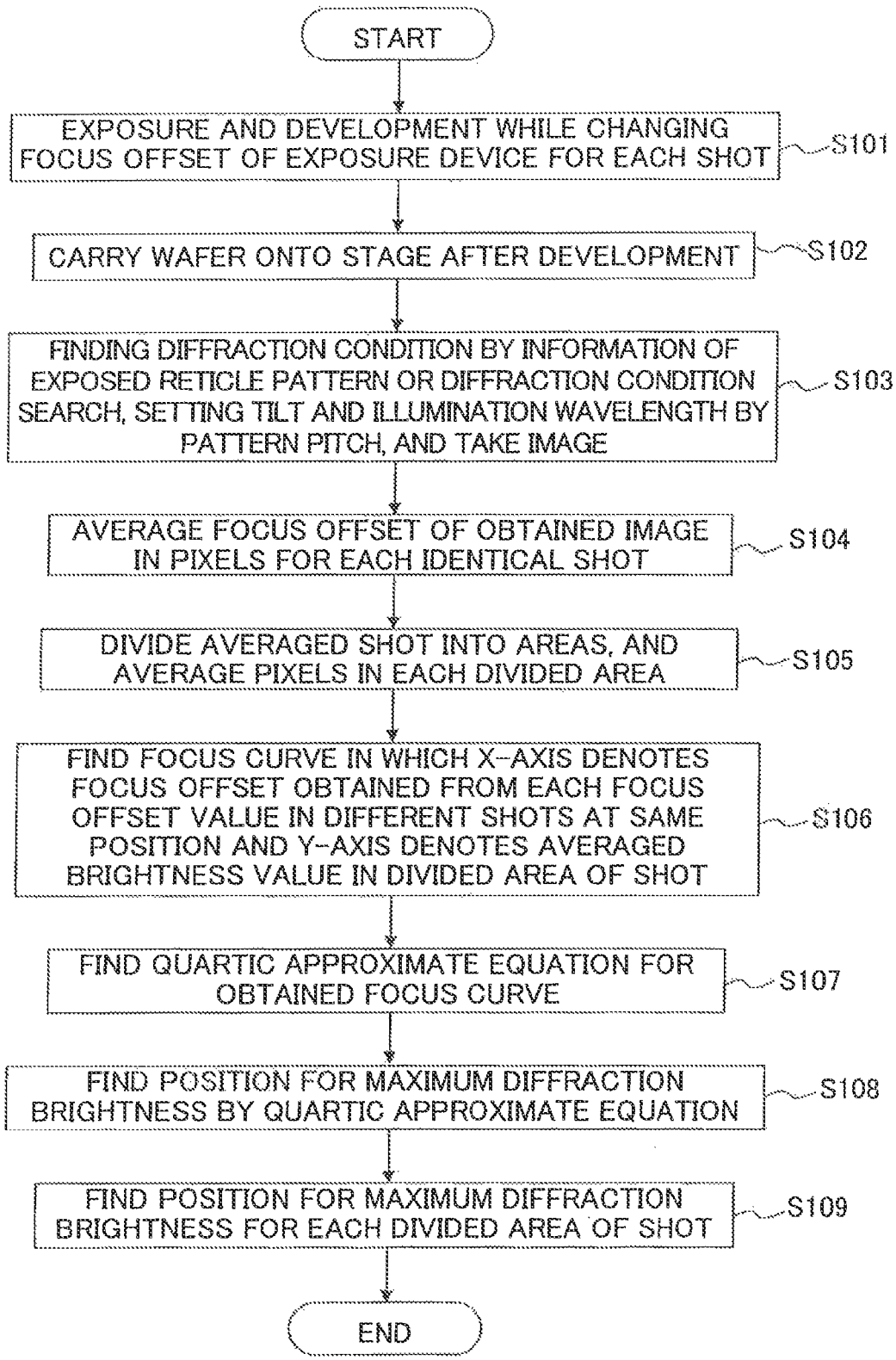
FIG. 6 is a flowchart showing a method for finding inclination of the image plane of an exposure device.

Hereinbelow, referring to the flowchart shown in FIG. 6, explanations will be made with respect to a method for finding the inclination of the image surface of the mask pattern projected and exposed by the exposure device 101. First, a wafer is produced with a repetitive pattern formed by changing the focus offset (predetermined) of the exposure device 101 (step S101). At this time, the process of exposure and development is carried out by changing the focus offset for each exposure shot, setting a plurality of shots with the same focus offset, and arranging the plurality of shots discretely (at random positions). Hereinbelow, such kind of wafer will be referred to as a condition-parameterizing wafer 10a (see FIGS. 7 and 8).

Here, the purpose of discretely arranging the shots with the same focus offset is to cancel out, for example, the difference in the resist condition occurring between the central side and the circumferential side of a wafer, and the influence of a so-called left-right difference and the like in scanning exposure. Further, since the resist film (photoresist) on the wafer is often formed by application of spin coat. As the resist solution spreads due to the spin, the solvent component vaporizes accordingly, and thereby the viscosity increases. For this reason, the film tends to become thicker to give rise to the difference in the resist condition between the central side and the circumferential side of the wafer. The so-called left-right difference is, for example, the difference in exposure while the reticle is moving in the positive X-direction (the wafer is moving in the negative X-direction), or the difference in exposure while the reticle is moving in the negative X-direction (the wafer is moving in the positive X-direction), when the scanning direction is taken as the X-direction.

Figure 7:
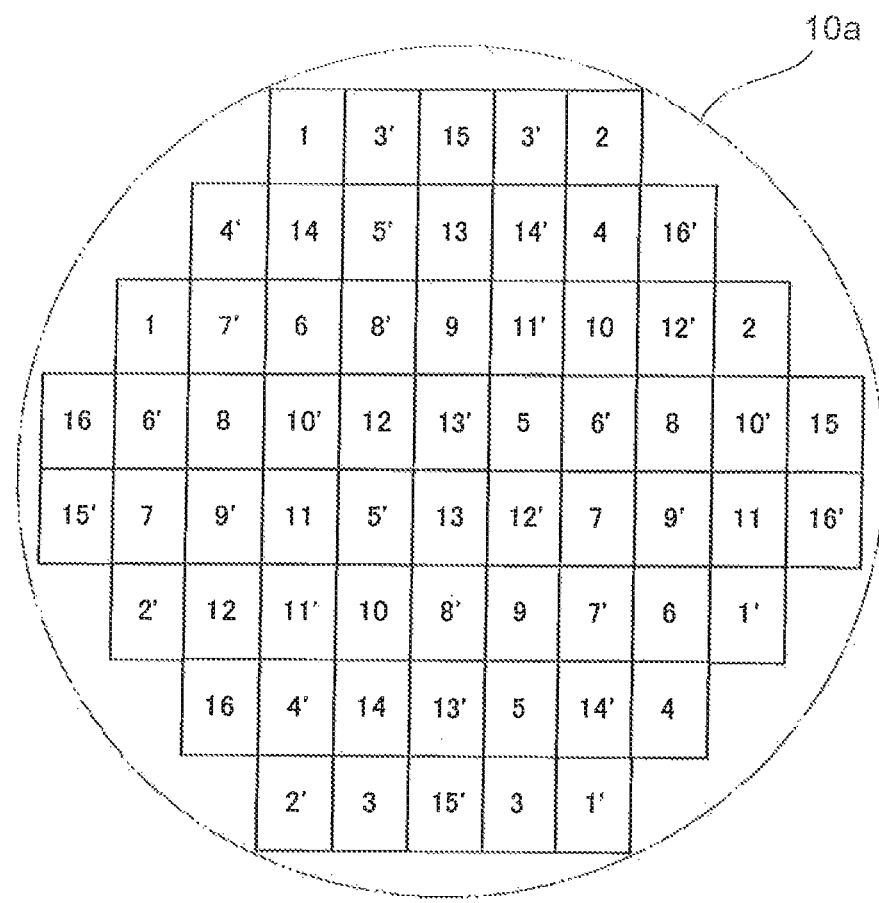
FIG. 7 is a table showing a focus offset set by a condition-parameterizing wafer.

The condition-parameterizing wafer 10a gradates the focus offset into 16 steps by 25 nm from −175 nm to +200 nm as shown in FIG. 7, for example. Further, in each shot of FIG. 7, the number (1 to 16) denotes the step of the focus offset gradated by 25 nm, where """ is assigned to the case with the same step but opposite scanning direction. For example, like the shot of the focus offset denoted by the number 12, it is possible to set an exposure to be carried out with the same focus offset in four places such as one shot at positive X-direction reticle movement/central side; one shot at positive X-direction reticle movement/circumferential side; one shot at negative X-direction reticle movement/central side; and one shot at negative X-direction reticle movement/circumferential side. Further for example, like the shot of the focus offset denoted by the number 15, it is possible to set an exposure to be carried out with the same focus offset with the center of the condition-parameterizing wafer 10a as the symmetrical axis in four places such as two snots at positive X-direction reticle movement/circumferential side; and two shots at negative X-direction reticle movement/circumferential side. In the example of FIG. 7, the condition-parameterizing wafer 10a is produced with totally 64 shots by four shots of each focus offset in 16 steps of the focus offset in the above manner by discretely arranging those shots.

Further, a plurality of condition-parameterizing wafers may as well be produced to find the focus curve. In this case, it is possible to set the shot arrangement according to each focus offset of each condition-parameterizing wafer to cancel out the influence due to other conditions than focus offset.

After producing the condition-parameterizing wafer 10a, in the same manner as in the case of diffraction inspection, the condition-parameterizing wafer 10a is carried onto the stage 5 (step S102). Next, still in the same manner as in the case of diffraction inspection, the illumination system 20 irradiates the surface of the condition-parameterizing wafer 10a with the illumination light beam, the imaging device 35 photoelectrical converts the diffraction image of the condition-parameterizing wafer 10a to generate an image signal and output the image signal to the image processing section 40 (step S103). At this time, the condition-parameterizing wafer 10a is set in the same manner as in the case of the diffraction inspection to find the diffraction condition by utilizing information of the exposed mask pattern or diffraction condition search, so as to obtain the diffracted light. The diffraction condition search refers to the function of changing the tilt angle of the stage 5 in a non-specular angular range in a stepwise manner and acquiring an image at each tilt angle to find the tilt angle for a brighter image, that is, the diffracted light is obtainable.

Figure 8:
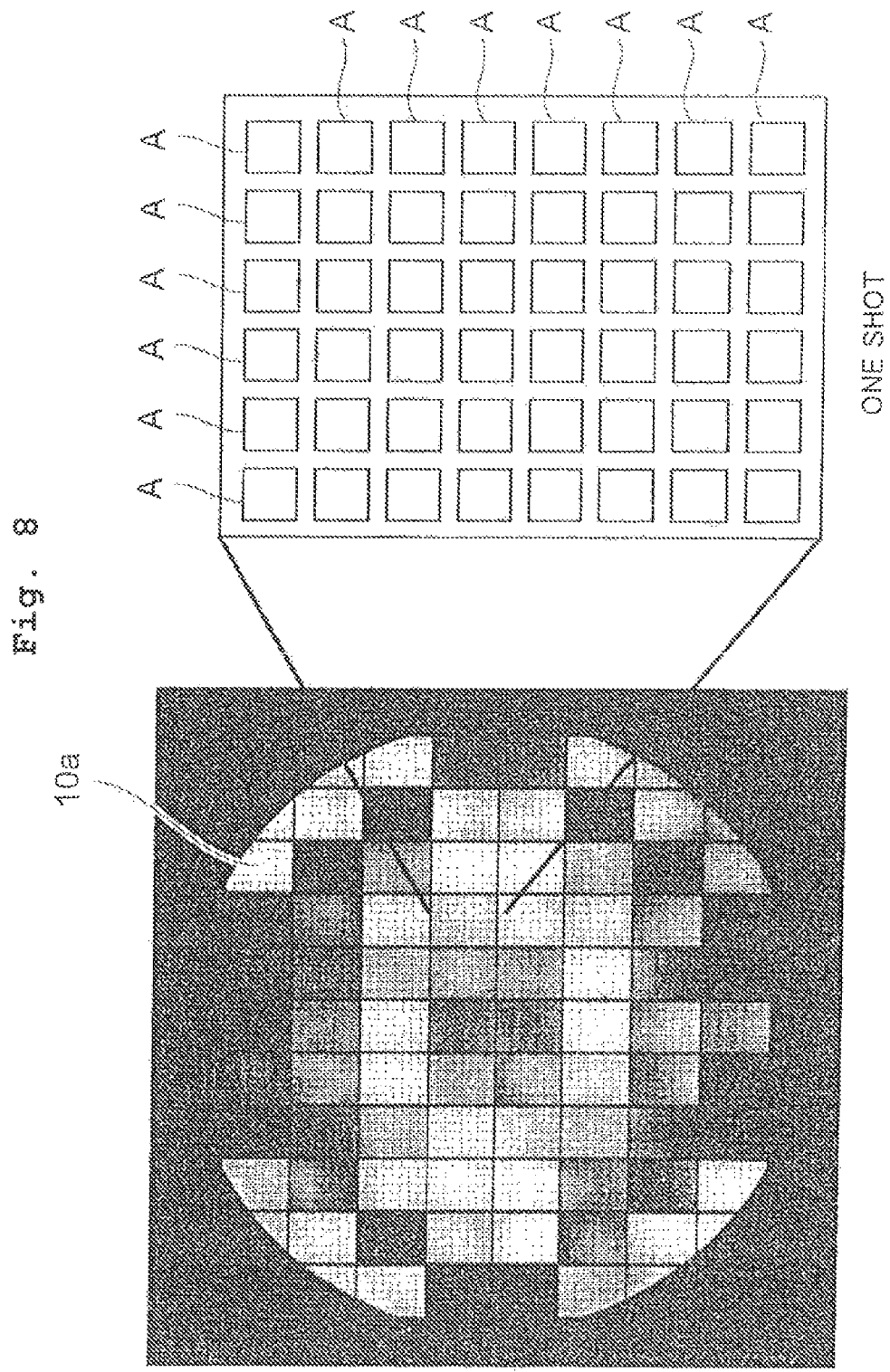
FIG. 8 shows an example of the condition-parameterizing wafer.

Next, based on the image signal of the condition-parameterizing wafer 10a inputted from the imaging device 35, the image processing section 40 generates a diffraction image of the condition-parameterizing wafer 10a, and carries out averaging of the signal intensity in the unit of pixels (the pixel group of the portion corresponding to each shot) for each shot of the same focus offset (step S104). Further, the portion determined to be defective in the diffraction inspection is excluded from the object of the above averaging. Next, with respect to all the shots obtained by the averaging, i.e., the shots different in focus offset from each other, the image processing section 40 finds the average value of the signal intensity (to be referred to as the average brightness hereinbelow for convenience), respectively, in a plurality of setting areas A (the areas encircled by a small rectangle) set in the shot as shown in FIG. 8 (step S105). In the process so far, with each of the plurality of setting areas A provided in the exposure shot, the average brightness can be obtained for each focus offset gradated by 25 nm into 16 steps from −175 nm to +200 nm.

Figure 9:
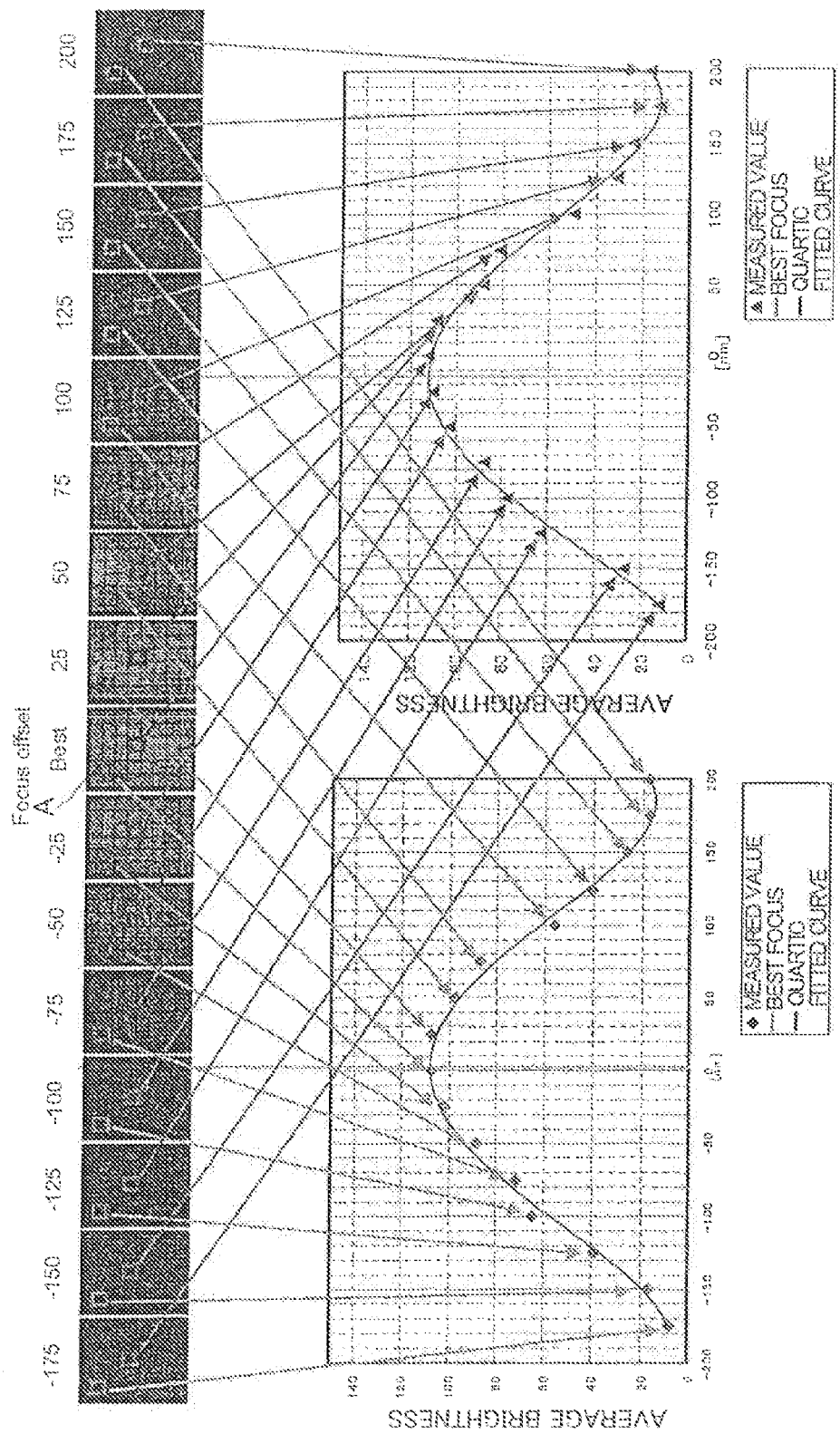
FIG. 9 shows an example of a focus curve.

Next, the image processing section 40 sends the averaged data to the inspection section 42 via the main control section 50. As shown in FIG. 9, the inspection section 42 finds the focus curve, that is, the graph showing a relationship between the average brightness in the setting area A of the same position in each shot (different in focus offset from each other) and the corresponding focus offset, for each setting area A having found the average brightness (step S106). After finding the focus curve, the inspection section 42 finds a fitted curve for the focus curve, respectively (step S107). According to the knowledge of the present inventors, it is possible to utilize a fourth-order function for the fitted curve. Further, the focus curve found here is referred to as the reference focus curve. It is possible to use any other functions for the fitted curve (for example, third-order function), as a fitting function.

Figure 10A:
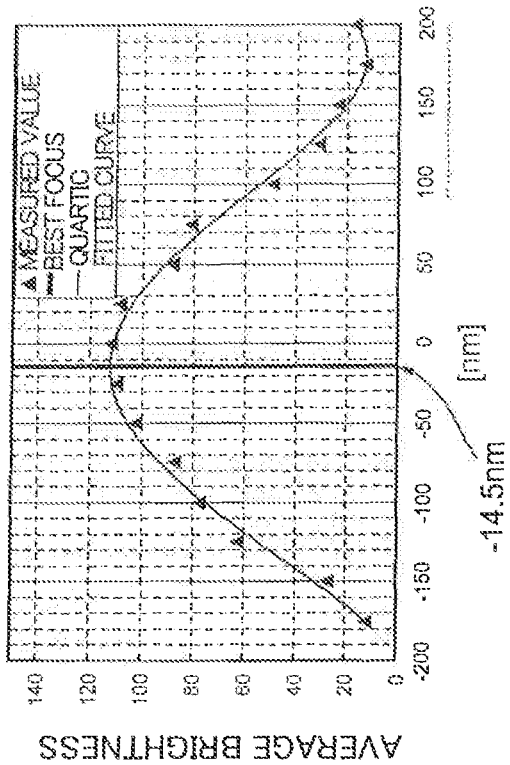
FIGS. 10A and 10B are graphs showing a relationship between the focus curve and the best focus.
Figure 10B:
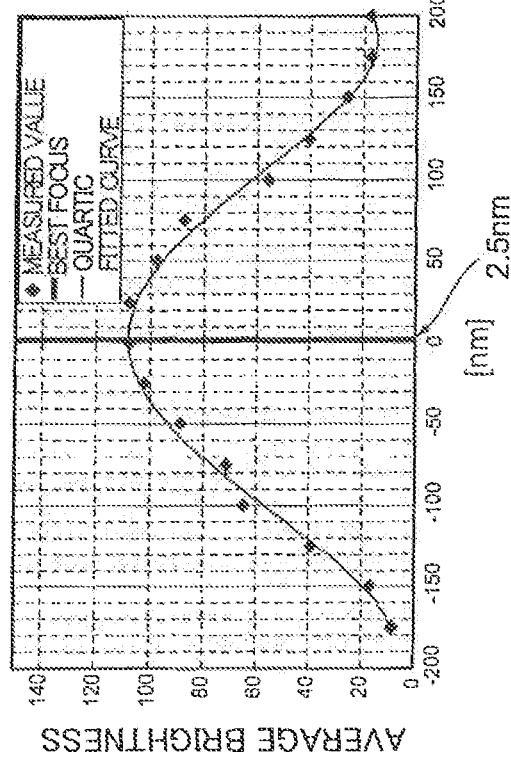
Figure 11:
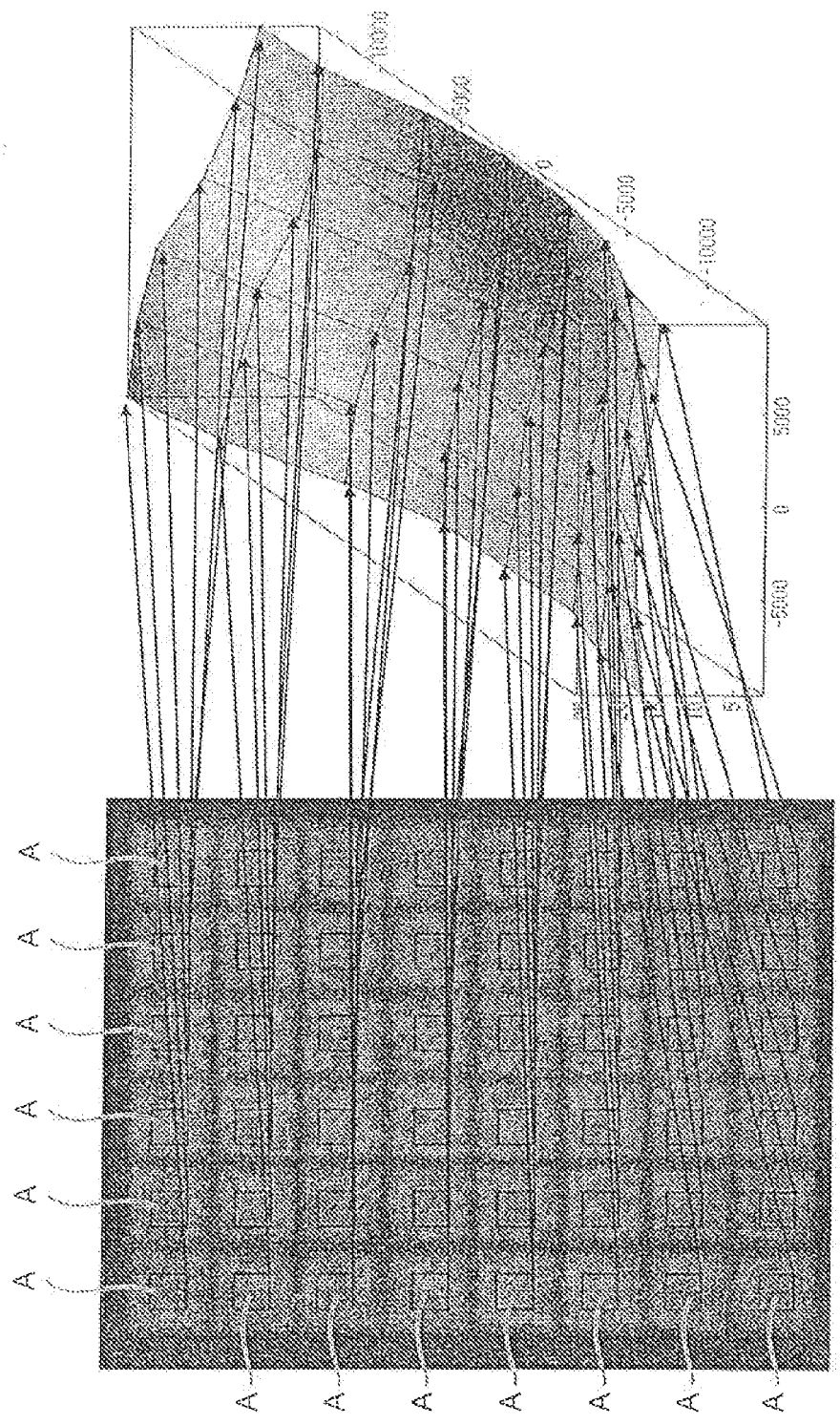
FIG. 11 shows a distribution of the focus offset within a shot.

Next, the inspection section 42 finds the focus offset for the average brightness to become maximum on the approximate focus curve, i.e., the maximum focus offset in the range of −175 nm to +200 nm (step S108). For example, in the case of the focus curve shown in FIG. 10A, the focus offset for the average brightness to become maximum is 2.5 nm. Further, for example, in the case of the focus curve shown in FIG. 10B, the focus offset for the average brightness to become maximum is −14.5 nm. At this time, the inspection section 42 finds the focus offset for the average brightness to become maximum for each setting area A (step S109). In so doing, as shown in FIG. 11, it is possible to find a distribution of the focus offset for the average brightness of diffracted light to become maximum in the shot.

By virtue of this, based on the distribution of the focus offset in the shot for the average brightness of diffracted light to become maximum, it is possible to (approximately) find the inclination of the focus offset of the slit (light) exposed by the exposure device 101 in the long-side direction (that is, the inclination amount of image plane), and the inclinations of the focus offset of the reticle stage and wafer stage of the exposure device 101 in the scanning direction, respectively. Even though the focus offset for the average brightness of diffracted light to become maximum is not the best focus, the relationship is substantially same between the focus offset and the average brightness of diffracted light because the pattern in the shot is analogous respectively, and the inclination of the image plane lies in a relative positional relation of each imaging point. Thereby, it is possible to find the inclination of the image plane by finding the maximum value of the average brightness. The inclination of the image plane found in this manner is outputted to the exposure device 101 from the main control section 50 via the signal output portion 60 after converted into parameters acceptable by the exposure device 101 such as image plane curvature, maximum and minimum values, the diagonal inclination and the like. These obtained parameters are reflected to the exposure by the exposure device 101. Further, the inclination of the image plane in the embodiment refers to the comprehensive inclination of the image plane with respect to the photoresist layer on the wafer due to the image plane inclination of the projection image by the projection lens in the exposure device 101, and the motion error of the reticle stage and the wafer stage. In this manner, the inspection section 42 also has a determination function.

Figure 12:
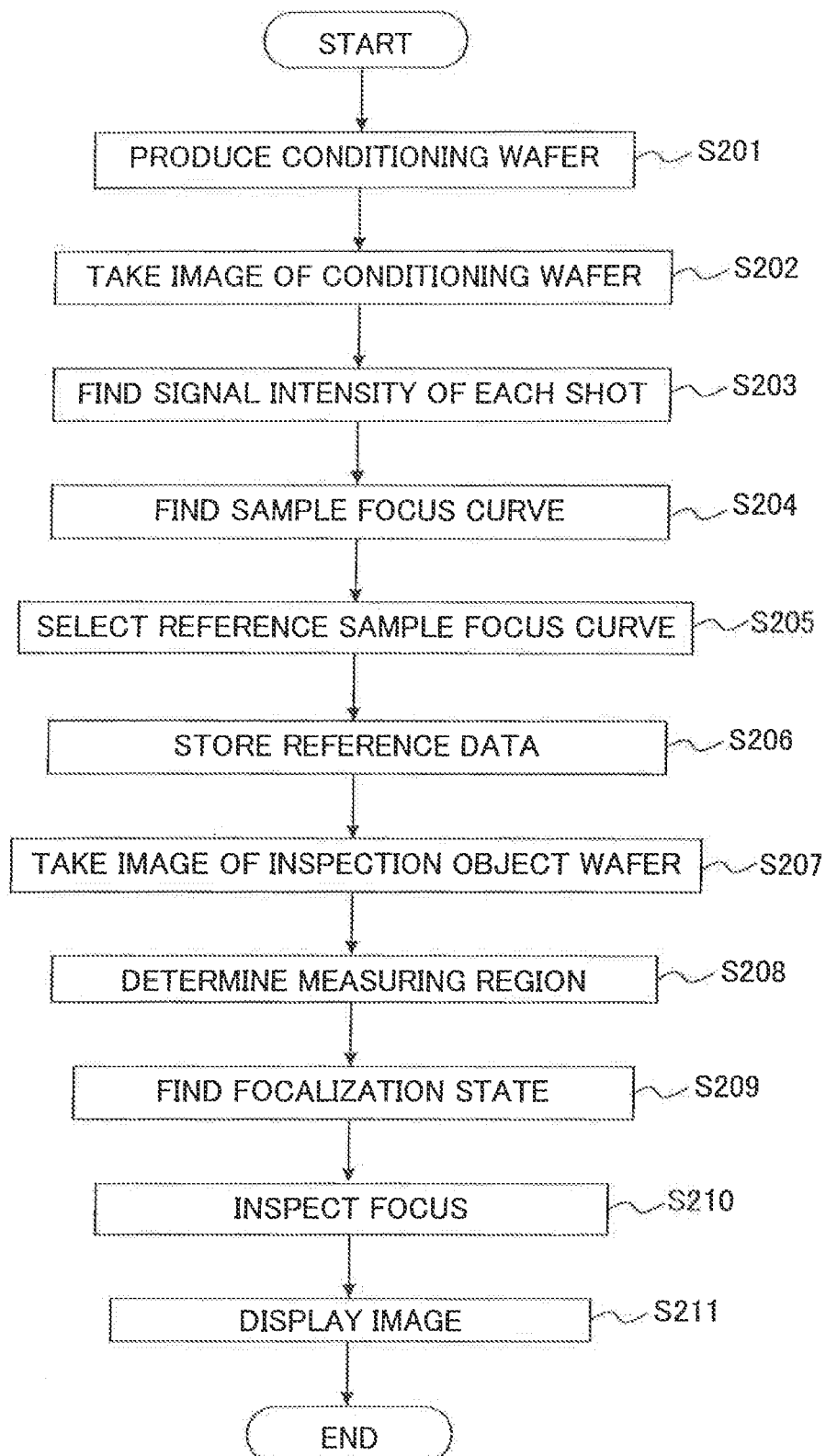
FIG. 12 is a flowchart showing a method for finding a focusing state in exposure due to the exposure device.

Further, the inspection section 42 is configured to be capable of finding the focusing state in exposure by the exposure device 101 from the diffraction image of the inspection object wafer 10, more specifically, the focusing variation state of the exposure device 101 for the entire surface of the wafer 10. Hereinbelow, referring to the flowchart shown in FIG. 12, explanations will be made with respect to a method for finding the focusing state in exposure by the exposure device 101. First, the inspection section 42 changes the focus offset and dose (exposure amount) of the exposure device 101 to matrix form to produce a condition-parameterizing wafer 10b with the repetitive pattern formed (see FIG. 13; step S201). At this time for example, the process of exposure and development is carried out by taking the central exposure shot of the condition-parameterizing wafer 10b as the best focus and best dose and changing the focus offset for each exposure shot aligning in the horizontal direction, while changing the dose for each exposure shot aligning in the vertical direction.

After producing the condition-parameterizing wafer 10b, the diffraction image of the condition-parameterizing wafer 10b is taken and obtained (step S202). In order to take the diffraction image of the condition-parameterizing wafer 10b, in the same manner as in the case of the diffraction inspection, first, the condition-parameterizing wafer 10b is carried onto the stage 5. Next, the illumination system 20 irradiates the surface of the condition-parameterizing wafer 10b with the illumination light beam, and the imaging device 35 photo-electrical converts the diffraction image of the condition-parameterizing wafer 10b to generate an image signal and output the image signal to the image processing section 40. Then, based on the image signal of the condition-parameterizing wafer 10b inputted from the imaging device 35, the image processing section 40 generates a diffraction image of the condition-parameterizing wafer 10b. At this time, with respect to a plurality of conditions determined by combining the azimuth angle, illumination wavelength, incidence angle, exit angle and the like of the wafer, that is, with respect to a plurality of diffraction conditions, a diffraction image of the condition-parameterizing wafer 10b is taken and obtained, respectively.

Further, when there are lower layers or lower layers unevenness in the repetitive pattern of the condition-parameterizing wafer 10b, it is possible to reduce the affect from the lower layers by utilizing a short-wavelength illumination light beam (for example, 248 nm, 313 nm and the like). Further, it is also possible to reduce the affect from the lower layers by inserting the illumination-side polarizing filter 26 setting the transmission axis in a predetermined azimuth into the optical path such that an s-polarized light beam is obtained as the illumination light. Further, it is still possible to reduce the affect from the lower layers by inserting the light-receiving-side polarizing filter 32 setting the transmission axis in a predetermined azimuth into the optical path such that only the s-polarized diffraction light beam can be received.

After taking the diffraction image of the condition-parameterizing wafer 10b, the image processing section 40 finds the signal intensity of each shot according to each diffraction image obtained under the plurality of diffraction conditions, respectively (step S203). At this time, the average signal intensity in the same shot is taken as the signal intensity of each shot. By virtue of this, it is possible to eliminate the influence of image plane inclination.

Next, the image processing section 40 sends the averaged diffraction image to the inspection section 42 via the main control section 50, and the inspection section 42 finds the focus curve (to be referred to as the sample focus curve hereinbelow as appropriate to distinguish it from the reference focus curve found in measuring the image plane inclination), for each different dose with respect to the diffraction image taken respectively under the plurality of diffraction conditions (step S204). The sample focus curve is a graph showing a relationship between the signal intensity of each shot and the corresponding focus offset (identical in dose but different in focus offset from each other). By virtue of this, for each different dose, it is possible to find a plurality of sample focus curves corresponding to the plurality of diffraction conditions, respectively. Further at this time, in the same manner as in the case of the reference focus curve, fitted curves are also found for the sample focus curves, respectively. According to the knowledge of the present inventors, it is possible to utilize a fourth-order function for the fitted curves. It is possible to use any other functions for the fitted curve (for example, third-order function), as a fitting function.

Next, the inspection section 42 selects at least two of sample focus curves utilized to find the focusing state in exposure from the plurality of sample focus curves (step S205). At this time for example, three sample focus curves are selected and determined to correspond to the diffraction conditions little affected by dose and lower layers variations (to be referred to as the reference sample focus curves hereinbelow as appropriate to distinguish them from other sample focus curves). In order to select and determine three reference sample focus curves, first, the inspection section 42 extracts a plurality of sample focus curves sensitive to focus variation from a plurality of sample focus curves. Next, the inspection section 42 extracts a plurality of sample focus curves less sensitive to dose variation from the sample focus curves sensitive to focus variation. Then, the inspection section 42 selects and determines three sample focus curves different from each other in curve peak or bottom position (focus offset) from the sample focus curves sensitive to focus variation but less sensitive to dose variation as the reference sample focus curves.

Figure 13:
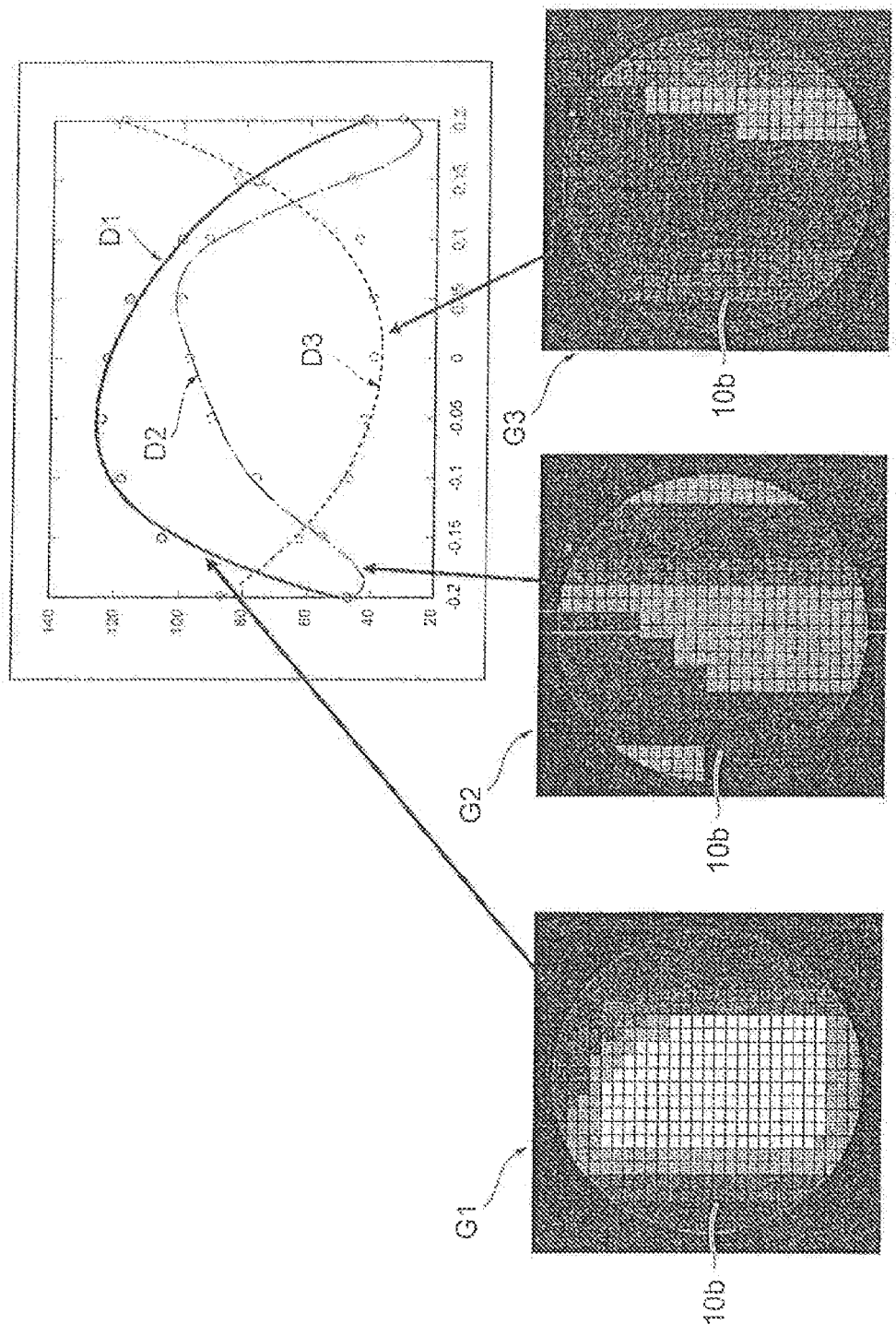
FIG. 13 shows diffraction images of a condition-parameterizing wafer taken under different conditions and a focus curve.

By virtue of this, it is possible to find a diffraction condition little affected by dose and lower layers variations, and three reference sample focus curves corresponding to the diffraction condition. FIG. 13 shows examples of the reference sample focus curves found in this manner. FIG. 13 shows three reference sample focus curves D1 to D3, as well as diffraction image G1 for obtaining the first reference sample focus curve D1, diffraction image G2 for obtaining the second reference sample focus curve D2 and diffraction image G3 for obtaining the third reference sample focus curve D3, respectively. Further, each of the diffraction images G1 to G3 shown in FIG. 13 is that of the condition-parameterizing wafer 10b taken by changing the diffraction condition. Further, each diffraction image may as well be taken by only changing the order of diffracted light but with the same pattern pitch, illumination wavelength, and the like.

After selecting and determining three reference sample focus curves, the image processing section 40 outputs the data with respect to the equation for the approximate curves of the determined reference sample focus curves to the storing section 45 to be stored as reference data (step S206). Further, being not limited to the equation for the fitted curves of the reference sample focus curves, the image processing section 40 may as well output a data map showing a relationship between the signal intensity and the focus offset found from the equation for the fitted curves to the storing section 45 to be stored as the reference data.

Further, when there are a plurality of exposure devices 101, then even for; exposure devices 101 of the same type, the NA (numerical aperture) may still be different for each device and for each switchable illumination conditions. Therefore, the reference data may be found for each exposure device or for each illumination condition, and may be stored into the storing section 45.

After the storing section 45 stores the reference data with respect to the three reference sample focus curves, the image processing section 40 obtains diffraction images of the inspection object wafer 10 (step S207). At this time, the diffraction images of the wafer 10 are obtained for the same three diffraction conditions as those for obtaining the reference sample focus corves, respectively.

After obtaining the diffraction images of the inspect ion object wafer 10, the image processing section 40 determines whether or not the region corresponding to each pixel is a measuring region in the shot based on the signal intensity of each pixel of the diffraction images (step S208), and excludes pixels corresponding to streets and the like from the measuring object.

After determining whether or not the region corresponding to each pixel is a measuring region in the shot, the image processing section 40 sends the diffraction image to the inspection section 42 via the main control section 50, and the inspection section 42 finds the focus variation state of the exposure device 101 with respect to the surface of the wafer 10 from the diffraction image of the inspection object wafer 10 (step S209). At this time, the focus offset of the exposure device 101 with respect to the surface of the wafer 10 for each predetermined pixel (in the unit of a single pixel or multiple pixels) is found based on the signal intensity of the diffraction image of the wafer 10 by utilizing the reference data stored in the storing section 45 (that is, the equation for the approximate curves of the reference sample focus curves or the data map). Further, in the case of finding the focus offset in the unit of multiple pixels, it is also necessary to distinguish the shot-nature defocus from the defocus due to foreign substances. Therefore, the region for finding the focus offset may be smaller than one shot (1/10 thereof, for example).

Figure 14:
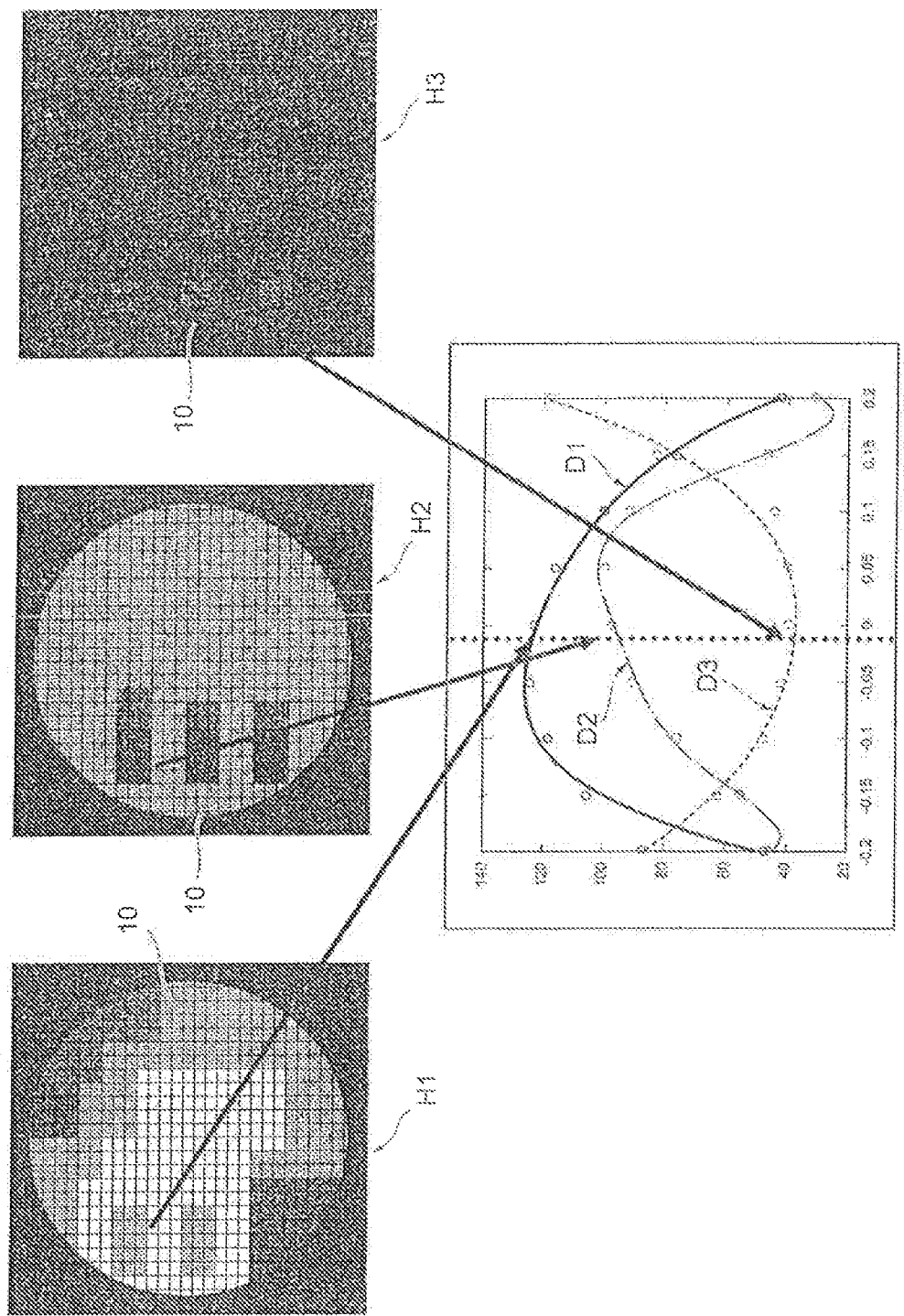
FIG. 14 shows an aspect of finding the focus offset from the diffraction images of a wafer taken under different conditions.

When finding the focus offset, since the storing section 45 stores the function (or data map) for the fitted curves of the reference sample focus curves corresponding respectively to three diffraction conditions, it is possible to find the focus offset, respectively, for each predetermined pixel based on the signal intensity of the diffraction images of the wafer 10 obtained respectively under the same condition. Further, because the focus curves are curve lines, a plurality of candidates of focus offset (possibly one, according to the condition) are calculated front the signal intensity of one diffraction image. On the other hand, by utilizing three reference sample focus curves D1 to D3 different from each other in curve peak or bottom position (focus offset), as shown in FIG. 14, the focus offset to be calculated is determined to be one. For example, the focus offset is found such that the square sum of the difference between the signal intensity under each condition and the approximate curve corresponding to that condition may become minimal. Further, focus offset may as well be adopted with a dose for the minimum square sum of the difference by preparing three reference sample focus curves D1 to D3 on each different dose. Further, the signal intensity may as well be weighted under the condition of relatively steep curve slope (that is, relatively high sensitivity to focus change). Further, with respect to pixels for which the minimum square sum of the difference exceeds a predetermined value, as an abnormal value, the result may as well not be adopted.

By virtue of this, it is possible to calculate the focus offset for each pixel on the entire surface of the wafer 10, and it is possible to determine the focus variation state of the exposure device 101 with respect to the surface of the wafer 10. Further, FIG. 14 shows three reference sample focus curves D1 to D3, as well as diffraction image H1 of the wafer 10 taken under the diffraction condition for obtaining the first reference sample focus curve D1, diffraction image H2 of the wafer 10 taken under the diffraction condition for obtaining the second reference sample focus curve D2, and diffraction image H3 of the wafer 10 taken under the diffraction condition for obtaining the third reference sample focus curve D3, respectively.

Figure 15:
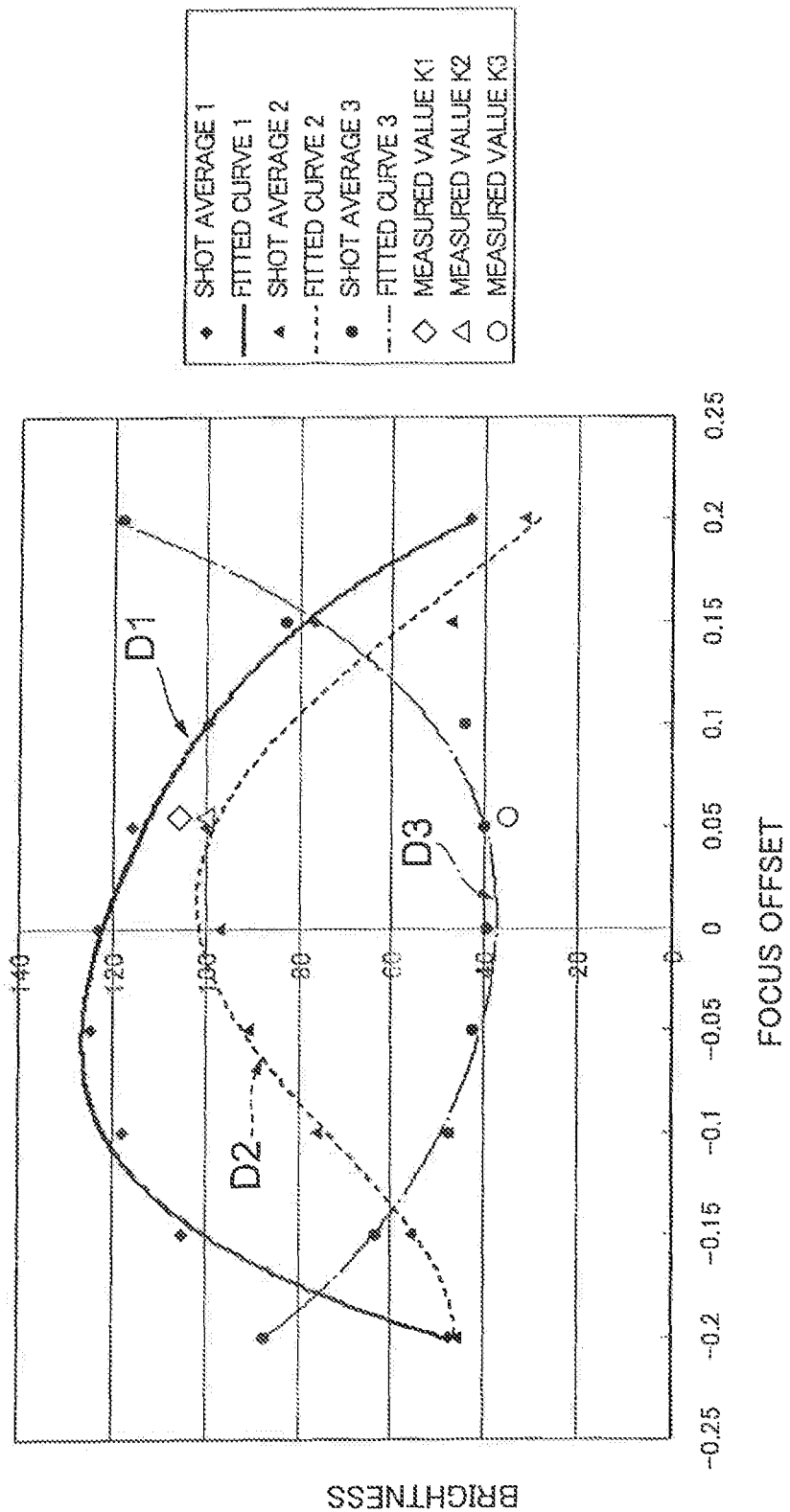
FIG. 15 is a graph showing a relationship between the focus curve and a measuring value of signal intensity.

Further, FIG. 15 shows a relationship between the reference sample focus curves D1 to D3 and the measuring value of each signal intensity of the focus offset for the minimum square sum of the difference (the first signal intensity K1, the second signal intensity K2 and the third signal intensity K3). It could be understood from FIG. 15 that there are high consistencies between the first detection signal (the first signal intensity K1) according to the diffracted light under the first diffraction condition from the repetitive pattern 12 detected by the imaging device 35 and the first reference data corresponding to this diffraction condition (the first reference sample focus curve D1), between the second detection signal (the second signal intensity K2) according to the diffracted light under the second diffraction condition from the repetitive pattern 12 and the second reference data corresponding to this diffraction condition (the second reference sample focus curve D2), and between the third detection signal (the third signal intensity K3) according to the diffracted light under the third diffraction condition from the repetitive pattern 12 and the third reference data corresponding to this diffraction condition (the third reference sample focus curve D3), respectively.

After finding the focus offset for each pixel on the entire surface of the wafer 10, the inspection section 42 inspects whether or not the found focus offset is abnormal (step S210). At this time, for example, the inspection section 42 determines it to be normal when the found focus offset is within the range of a predetermined threshold value, or abnormal when the found focus offset is out of the range of the predetermined threshold value. It is possible to provide the storing section independently from the surface inspection apparatus 1, at an outside thereof (for example, in the control room of the semiconductor production lines). In this case, it is possible to configure the storing section so that the fitted curves of the reference sample focus curves (or data maps) are retrieved from the storing section via the line (wired or wireless).

Figure 16:
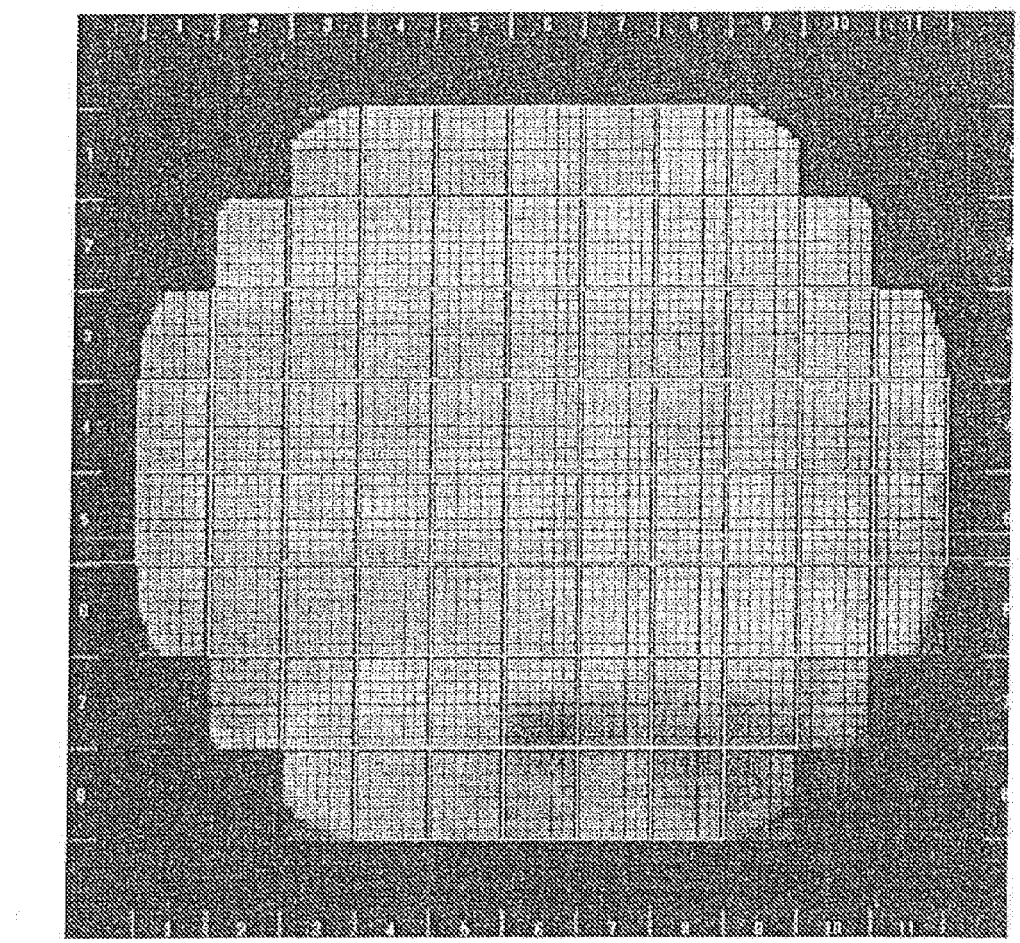
FIG. 16 shows a variation state of focus with respect to the wafer surface.

After inspecting whether or not the focus offset is abnormal, the image processing section 40 generates an image for the wafer 10 having converted the focus offset found for each pixel into the signal intensity with each corresponding pixel, and displays the image with the inspection result of the focus offset and the like on the image display device (not shown) (step S211). Further, being not limited to the surface inspection apparatus 1 of the embodiment, it is also possible to utilize an image display device provided outside the inspection apparatus (for example, in the control room of a semiconductor production line and the like) and connected to the inspection apparatus. Here, FIG. 16 shows an example of the image of the wafer 10 having converted the focus offset into signal intensity. Further, the image shown in FIG. 16 is not limited to a black and white image but may as well be displayed in color.

In this manner, according the surface inspection apparatus 1 of the embodiment, the inspection section 42 determines the focusing state in exposure (processing condition) for the repetitive pattern 12 in the wafer 10 based on the consistency between the first detection signal (the first signal intensity K1) detected by the imaging device 35 and the first reference data (the first reference sample focus curve D1), the consistency between the second detection signal (the second signal intensity K2) and the second reference data (the second, reference sample focus curve D2), and the consistency between the third detection signal (the third signal intensity K3) and the third reference data (the third reference sample focus curve D3). By virtue of this, it is possible to find the focusing state in exposure based on the image of the wafer 10 exposed with a mask pattern utilized for actual exposure. Therefore, like the case of utilizing a dedicated mask substrate, because no time is needed for operations to provide conditions for parameters necessary for measurement, it is possible to measure the focusing state in exposure in a short time. Further, it is possible to utilize a pattern used for actual devices instead of a dedicated mask pattern and, furthermore, because the illumination condition for the exposure device 101 is not restricted, it is possible to measure the focusing state in exposure with a high precision.

Further at this time, since it is possible to utilize the three reference data (the reference sample focus curves D1 to D3) different from each other in curve peak or bottom position (focus offset), i.e. different in the manner of change in detection signal with respect to focus variation, as described above, the focus offset to be calculated is determined to be one. Therefore, it is possible to measure the focusing state with a higher precision.

Further, since it is possible to utilize the three reference data (the reference sample focus curves D1 to D3) sensitive to focus variation but less sensitive to dose (exposure amount) variation, the sensitivity to focus variation (change in detection signal) is higher than that to the dose variation (change in detection signal). Therefore, it is possible to eliminate the influence due to the change in dose, and thus it is possible to measure the focusing state in exposure with a higher precision.

Further, the stage 5 is configured to be tiltable about the axis through the support plane for supporting the wafer 10, that is, to be rotatable about the axis approximately perpendicular to the propagating direction of the illumination light beam and approximately parallel to the plane supporting the wafer 10. By virtue of this, because it is possible to change the diffraction condition (the incidence angle of the illumination light beam and the like) in a short time, it is possible to take a plurality of diffraction images under different diffraction conditions in a short time. Hence, the focusing state in exposure can be measured in a shorter time.

Further, in the above embodiment, although the focusing state in exposure (processing condition) for the repetitive pattern 12 in the wafer 10 is determined by utilizing three reference data (reference sample focus curves D1 to D3), the present teaching is not limited to this. For example, two or five kinds of reference data may as well be utilized. The focusing state in exposure may be determined by utilizing at least two kinds of reference data different in the manner of change of the detection signal with respect to focus variation.

In the above embodiment, although inspection is carried out on the repetitive pattern 12 formed through exposure in the resist film on the wafer 10, the present teaching is not limited to this. For example, the inspection may as well be carried out on the pattern after etching. By virtue of this, not only the focusing state in exposure, but the defect (abnormity) in etching can also be detected.

In the above embodiment, in addition to the diffraction image of the condition-parameterizing wafer 10b, the polarization image (PER image) of the condition-parameterizing wafer 10b may as well be utilized, by the same method as in the aforementioned case, to find a plurality of sample focus curves due to the polarized light determined by the wafer azimuth angle, illumination wavelength and the like for each different dose and, therefrom, select and determine a plurality of reference sample focus curves due to the polarized light. By virtue of this, the reference sample focus curves due to the polarized light (reference data) can be utilized to find the focus variation state of the exposure device 101 with respect to the surface of the wafer 10 from the signal intensity of the polarization image taken by the imaging device 35. In this case, because detection conditions increase compared with the case of the diffraction image only, it is possible to measure the focusing state in exposure with a higher precision. Further, with the polarized light, because the focus offset can be considered to be the best focus as the signal intensity becomes maximum on the focus curve, it is possible to easily know the focus offset for the best focus. For example, the diffraction image and the polarization image may be utilized in a combined manner such as the first detection signal utilizes the diffraction image, and the second detection signal utilizes the polarization image.

In the above embodiment, although the focusing state in exposure with respect to the repetitive pattern 12 in the wafer 10 is determined by utilizing three kinds of reference data sensitive to focus variation but less sensitive to dose variation (the reference sample focus curves D1 to D3), it is also possible to determine the dose in exposure with respect to the repetitive pattern 12 in the wafer 10 by extracting a plurality of sample focus curves sensitive to dose variation taut less sensitive to focus variation from a plurality of sample focus curves and utilizing the sample dose curves obtained in the same manner by substituting dose for the focus of these sample focus curves.

In the above embodiment, it is possible to output the focus variation state (focus offset) of the exposure device 101 with respect to the surface of the wafer 10 found by the inspection section 42 to the exposure device 101 from the main control section 50 via the signal output portion 60, and feed back to the setting of the exposure device 101. Hereinbelow, referring to FIGS. 17 and 18, explanations will foe made with respect to an exposure system including the surface inspection apparatus 1 described above. This exposure system 100 is configured to include the exposure device 101 configured to project and expose a predetermined mask pattern (repetitive pattern) onto the surface of the wafer 10 to which resist is applied, and the surface inspection apparatus 1 configured to inspect the wafer 10 with the repetitive pattern 12 formed in the surface through an exposure process due to the exposure device 101, a development process due to a development device (not shown), and the like.

Figure 17:
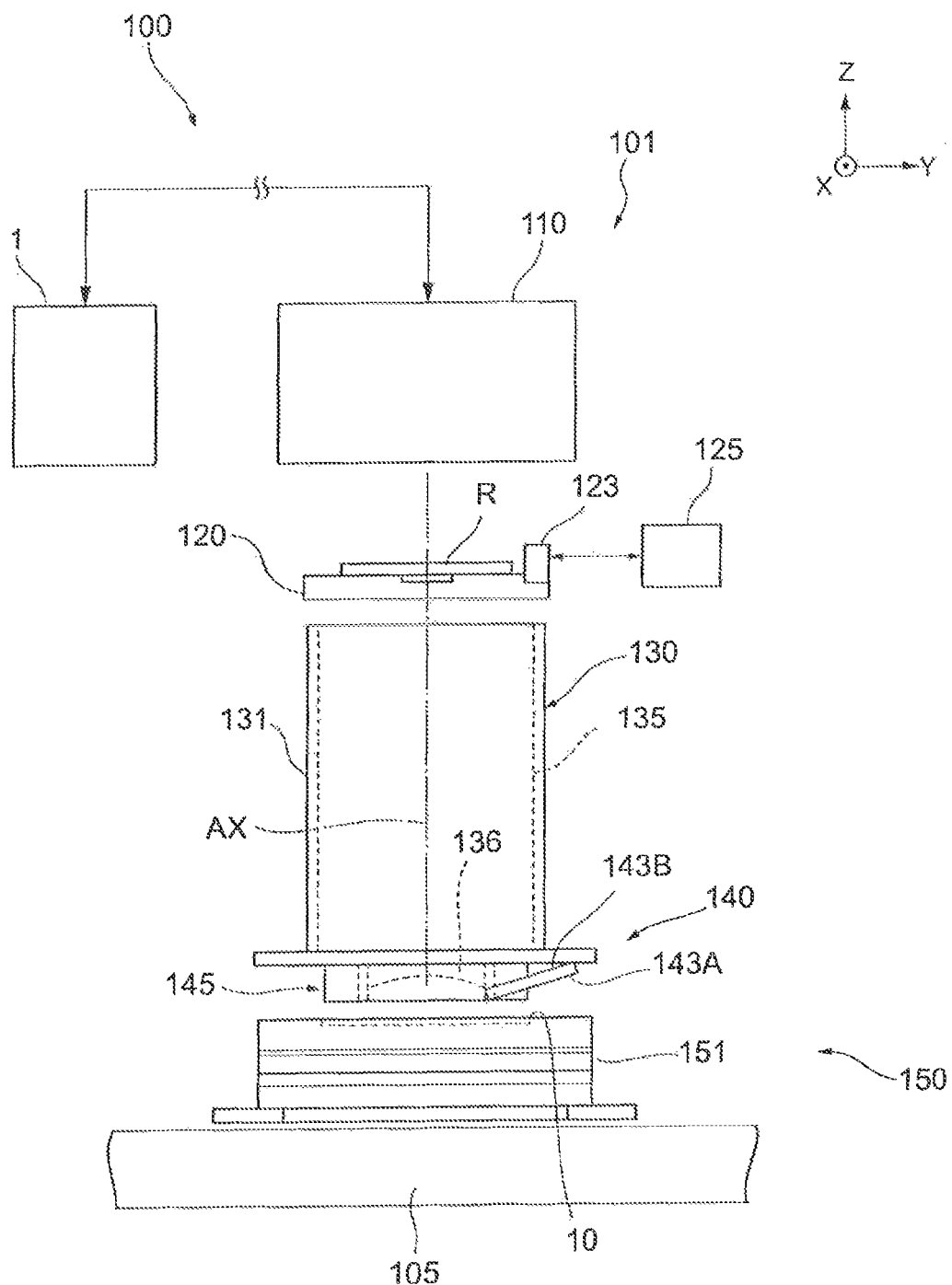
FIG. 17 is a schematic configuration diagram of an exposure system.
Figure 18:
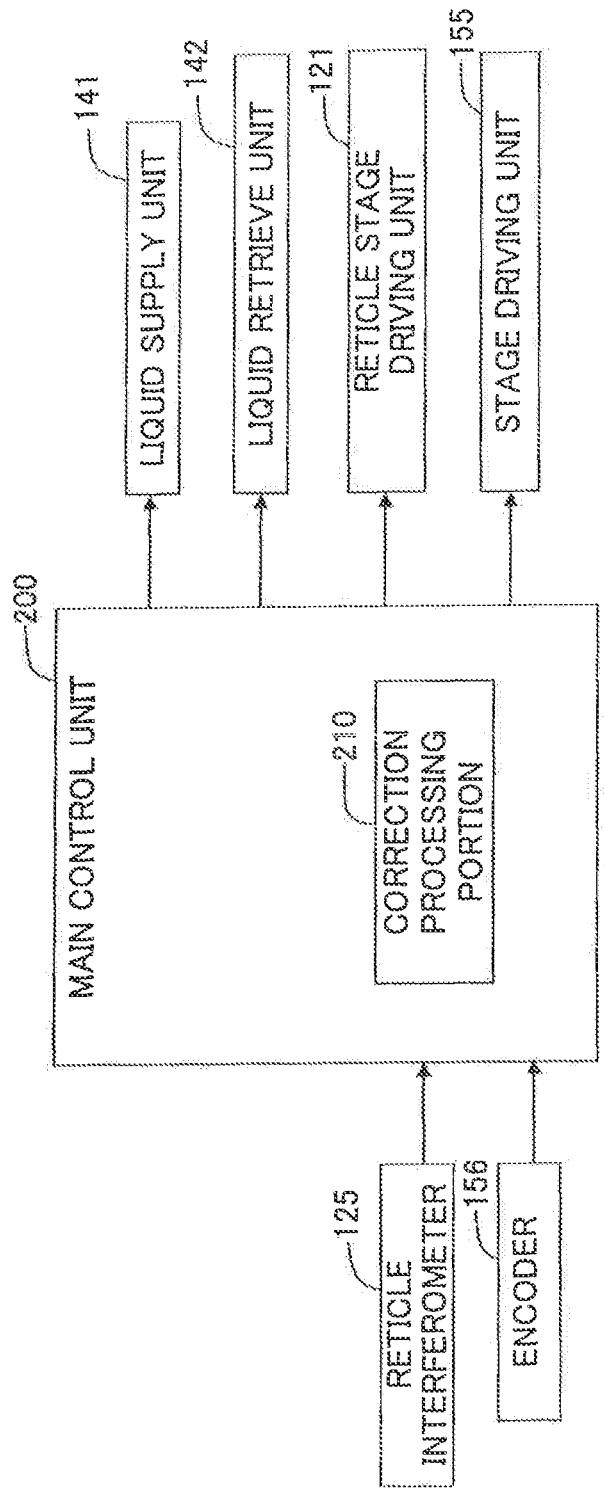
FIG. 18 is a control block diagram of the exposure device.

The exposure device 101 is configured, as shown in FIG. 17, to include an illumination system 110, a reticle stage 120, a projection unit 130, a local inversion device 140, a stage device 150, and a main control device 200 (see FIG. 18). Further, explanations will be made hereinbelow with the directions indicated by arrow marks X, Y and Z shown in FIG. 17 as the X-axis direction, Y-axis direction and Z-axis direction, respectively.

Detailed illustration being omitted, the illumination system 110 has a light source, a luminance uniformization optical system including an optical integrator and the like, and an illumination optical system including a reticle blind and the like, and is configured to illuminate a slit-shaped illumination region on a reticle R defined by the reticle blind with an illumination light beam (exposure light beam) of an approximately uniform luminance. As the illumination light, for example, ArF excimer laser light (wavelength 193 nm) is utilized.

On the reticle stage 120, the reticle R (photomask) is fixed and held by vacuum suction, for example, with a predetermined pattern (a line pattern, for example) formed in its pattern surface (the lower surface in FIG. 17). The reticle stage 120 is configured to be movable in the X-Y plane by a reticle stage drive device 121 including such as a linear motor and the like (see FIG. 18), and movable at a predetermined scanning speed in the scanning direction (the Y-axis direction here).

A reticle interferometer 125 detects positional information of the reticle stage 120 in the X-Y plane (including rotational information in the rotation direction about Z-axis) via a first reflector 123 having a reflection surface perpendicular to Y-axis and a second reflector (not shown) having a reflection surface perpendicular to X-axis, provided, on the reticle stage 120. The positional information detected by the reticle interferometer 125 is sent to the main control device 200, which controls the position (and the moving speed) of the reticle stage 120 via the reticle stage drive device 121 based on this positional information.

The projection unit 130 is arranged below the reticle stage 120 and configured to have a lens barrel 131, and a projection optical system 135 held inside the lens barrel 131. The projection optical system 135 is configured to have a plurality of optical elements (lens elements) aligned along the optical axis AX of illumination light, and have a predetermined projection magnification (for example, ¼, ⅕, ⅛, or the like) on both telecentric sides. Therefore, when the illumination light beam emitted from the illumination system 110 illuminates the illumination region on the reticle R, by virtue of the illumination light beam transmitted through the reticle R arranged such that the objective surface of the projection optical system 135 is approximately consistent with the pattern surface, a diminished pattern image of the reticle R within the illumination region is formed in the exposure region on the wafer 10 arranged on the imaging plane side of the projection optical system 135 (the region conjugative to the illumination region on the reticle R) via the projection optical system 135. Then, by synchronously driving the reticle stage 120 and the stage device 150 for holding the wafer 10, the reticle R is moved in the scanning direction with respect to the illumination region (the Y-axis direction), while the wafer 10 is also moved in the scanning direction with respect to the exposure region (the Y-axis direction). Accordingly, a scanning exposure is carried out in one shot region on the wafer 10, and thus the pattern (mask pattern) of the reticle R is transferred to that shot region.

In the exposure device 101, the local immersion device 140 is provided to carry out exposure in an immersion method. As shown in FIGS. 17 and 18, the local immersion device 140 is configured to have a liquid supply device 141, a liquid retrieve device 142, a liquid supply pipe 143A, a liquid retrieve pipe 143B, and a nozzle unit 145. The nozzle unit 145 is supported by a frame member (a member (not shown) constituting the exposure device 101) configured to support the projection unit 130 in such a manner as enclosing the periphery of the lower end of the lens barrel 131 for holding the optical element closest to the imaging plane (the wafer side) constituting the projection optical system 135, i.e., the foremost lens 136 in the present case. Further, the nozzle unit 145 is set as shown in FIG. 17 such that its lower-end surface lies in almost the same plane with the lower-end surface of the foremost lens 136.

Detailed illustration being omitted, the liquid supply device 141 is configured to have a tank storing liquid, a pressure pump, a temperature controller, and a valve configured to control liquid flow rate, and is connected to the nozzle unit 145 through the liquid supply pipe 143A. Again detailed illustration being omitted, the liquid retrieve device 142 is configured to have a tank storing retrieved liquid, a suction pump, and a valve configured to control liquid flow rate, and is connected to the nozzle unit 145 through the liquid retrieve pipe 143B.

As shown in FIG. 18, the main control device 200 controls the operation of the liquid supply device 141 to supply liquid (pure water, for example) to the portion between the foremost lens 136 and the wafer 10 through the liquid supply pipe 143A, while controlling the operation of the liquid retrieve device 142 to retrieve the liquid from the portion between the foremost lens 136 and the wafer 10 through the liquid retrieve pipe 143B. At this time, the main control device 200 controls the operations of the liquid supply device 141 and liquid retrieve device 142 such that the supplied liquid amount is constantly equal to the retrieved liquid amount. Therefore, between the foremost lens 136 and the wafer 10, a certain amount of liquid is constantly exchanged and maintained, whereby an immersion region (immersion space) is formed. In this manner, the exposure device 101 exposes the wafer 10 by irradiating the wafer 10 with the illumination light beam via the liquid forming the immersion region.

The stage device 150 is configured to have a wafer stage 151 arranged below the projection unit 130, and a stage drive device 155 for driving the wafer stage 151 (see FIG. 18). The wafer stage 151 is supported in a levitated manner by an air slide (not shown) above a base member 105 with a clearance or a few micrometers, and configured to held the wafer 10 on the upper surface of the wafer stage 151 by vacuum suction. Further, the wafer stage 151 is movable along the upper surface of the base member 105 within the X-Y plane by means of a motor constituting the stage drive device 155.

An encoder 156 (see FIG. 18) detects positional information of the wafer stage 151 in the X-Y plane. The positional information detected by the encoder 156 is sent to the main control device 200, which controls the position (and the moving speed) of the wafer stage 151 via the stage drive device 155 based on this positional information.

In the exposure device 101 configured in the above manner, when the illumination light beam emitted from the illumination system 110 illuminates the illumination region on the reticle R, by virtue of the illumination light beam transmitted through the reticle R arranged such that the objective surface of the optical projection system 135 is approximately consistent with the pattern surface, a diminished pattern image of the reticle R within the illumination region is formed in the exposure region on the wafer 10 supported on the wafer stage 151 and arranged on the imaging plane side of the projection optical system 135 (the region conjugative to the illumination region on the reticle R) via the projection optical system 135. Then, by synchronously driving the reticle stage 120 and the wafer stage 151 for supporting the wafer 10, the reticle R is moved in the scanning direction with respect to the illumination region (the Y-axis direction), while the water 10 is also moved in the scanning direction with respect, to the exposure region (the Y-axis direction). Accordingly, a scanning exposure is carried out in one shot region on the wafer 10, and thus the pattern of the reticle R is transferred to that shot region.

In this manner, after the exposure process is carried out with the exposure device 101, through the development process and the like with the developing device (not shown), the surface inspection apparatus 1 in accordance with the aforementioned embodiment carries out the surface inspection of the wafer 10 with the repetitive pattern 12 formed in the surface. Further at this time, the inspection section 42 of the surface inspection apparatus 1 finds the focus variation state of the exposure device 101 with respect to the surface of the wafer 10 as described hereinbefore, and outputs the information about the found focus variation state (focus offset) to the exposure device 101 from the main control section 50 through the signal output portion 60, a connecting cable (not shown) and the like. Then, a correction processing portion 210 provided in the main control device 200 of the exposure device 101 corrects various setting parameters and arrangement condition of the optical element about the focusing of the exposure device 101 based on the focus variation state of the exposure device 101 inputted from the surface inspection apparatus 1 such that the focusing state of the exposure device 101 becomes constant with respect to the surface of the wafer 10.

By virtue of the above configuration, according to the exposure system 100 of the embodiment, because the focus setting of the exposure device 101 is corrected according to the focusing state in exposure inputted from the surface inspection apparatus 1 in accordance with the aforementioned embodiment, it is possible to measure the focusing state in exposure in a short time with a high precision. Therefore, the correction can be made based on the focusing state of a higher precision, thereby allowing the focus of the exposure device 101 to be set more properly.

Next, referring to FIG. 19, explanations will be made with respect to a method for producing a semiconductor device utilizing such kind of exposure system 100. The semiconductor device (not shown) is produced through a design process for designing the function and performance of the device (step S301), a reticle producing process for producing a reticle based on the design process (step S302), a wafer producing process for producing a wafer from a silicon material (step S303), a lithography process for transferring a reticle pattern to the wafer by exposure and the like (including an exposure process, a development process and the like; step S304), an assembly process for assembling the device (including a dicing process, a bonding process, a packaging process and the like; step S305), an inspection process for inspecting the device (step S306), and the like.

Hereinbelow, referring to FIG. 20, the lithography process will be explained in detail. First, a wafer is prepared (step S401), and a coating applicator (not shown) such as a spin coater and the like is utilized to applying resist to the wafer surface to a predetermined thickness (step S402). At this time, film formation is carried out on the coated wafer by vaporizing the solvent ingredient in the resist with a drying device in the coating applicator. The wafer with the formed resist film is carried to the exposure device 101 by a carrier device (not shown) (step S403). The wafer carried to the exposure device 101 is aligned by an alignment device included in the exposure device 101 (step S404). The aligned wafer is exposed to the diminished reticle pattern (step S405). The exposed wafer is transported to a development device (not shown) from the exposure device 101 to be developed (step S406). The developed wafer is set in the surface inspection apparatus 1, which is then to find the focusing state of the exposure device 101 as described hereinbefore and, meanwhile, inspect the pattern formed in the wafer by carrying out diffraction and polarization inspections (step S407). When a defect (abnormity) is inspected to be more than a predetermined standard, then the wafer with the defect is passed to a reworking (refabrication) process, while a wafer without exceeding the defect (abnormity) standard is to undergo an aftertreatment such as etching processing and the like. Further, the focusing state of the exposure device 101 found in step S407 is fed back to the exposure device 101 for the correction of focus setting (step S408).

In the method of the present embodiment for producing a semiconductor device, the exposure system 100 according to the aforementioned embodiment is utilized to carry out the exposure of the pattern. That is, as described hereinbefore, after the exposure device 101 carries out the exposure process, through the development process by the development device (not shown) and the like, the surface inspection apparatus 1 carries out the surface inspection on the wafer 10 with the repetitive pattern 12 formed in its surface. At this time, the surface inspection apparatus 1 determines the focusing state in exposure, while the exposure device 101 corrects the focus setting for the exposure device 101 according to the focusing state in exposure inputted from the surface inspection apparatus 1. In this manner, according to the semiconductor device production method of the embodiment, it is possible to measure the focusing state in exposure in a short time with a high precision. Therefore, it becomes possible to set the focus of the exposure device 101 in a more proper manner, thereby allowing high-integrated semiconductor devices to be fabricated with high productivity.

In the above embodiment, although the exposure device 101 of the liquid immersion type having the local immersion device 140 is used as the exposure device, the present teaching is not limited to this. The present teaching can be applicable to the non-liquid immersion type exposure device.

What is claimed is:

1. A method for inspecting a surface of a substrate comprising:
    illuminating, with an illumination light beam, a predetermined region of a surface of a substrate having a pattern processed under a predetermined processing condition;
    detecting a first detection signal according to a first light beam propagating in a first direction from the pattern within the predetermined region and a second detection signal according to a second light beam propagating in a second direction different from the first direction;
    providing a first reference data indicating a relationship between the first detection signal and a plurality of predetermined processing conditions, and a second reference data indicating a relationship between the second detection signal and the plurality of predetermined processing conditions, with respect to at least one substrate having a plurality of patterns processed under the plurality of predetermined processing conditions; and
    determining a processing condition for the pattern in the substrate as inspection object based on consistency between the first detection signal detected from the inspection object substrate and the first reference data, and consistency between the second detection signal detected from the inspection object substrate and the second reference data.

2. The method for inspecting the surface according to claim 1, wherein the pattern is provided through exposures performed in the predetermined region; the determined processing condition is at least one of a focusing state and an exposure amount in the exposures; and change in the first detection signal with respect to change in the processing condition is opposite to change in the second detection signal with respect to the change in the processing condition.

3. The method for inspecting the surface according to claim 1, wherein the determined processing condition is the focusing state; and the change in the first detection signal and the change in the second detection signal with respect to change in the focusing state are greater than those with respect to change in the exposure amount.

4. The method for inspecting the surface according to claim 1, wherein providing the first and second reference data includes: storing the first and second reference data; and retrieving the stored fist and second reference data.

5. The method for inspecting the surface according to claim 1, wherein at least one of the first detection signal and the second detection signal is based on diffracted light beam.

6. The method for inspecting the surface according to claim 5, wherein the first and second direction are directions in which diffracted light beams having different orders with each other and being generated at the pattern within the predetermined region propagate.

7. The method for inspecting the surface according to claim 1, wherein at least one of the first detection signal and the second detection signal is based on a predetermined polarization component.

8. The method for inspecting the surface according to claim 1, further comprising:
    detecting a third detection signal according to a third light beam propagating in a third direction different from both the first direction and the second direction; and
    storing a third reference data indicating a relationship between the third detection signal and the plurality of predetermined processing conditions with respect to the substrate having the plurality of patterns,
    determining the processing condition for the pattern in the inspection object substrate includes determining, the processing condition based on the consistency between the first detection signal detected from the inspection object substrate and the first reference data, the consistency between the second detection signal detected from the inspection object substrate and the second reference data, and consistency between the third detection signal detected from the inspection object substrate and the third reference data.

9. A method for producing a semiconductor device comprising:
    performing a lithography in which a predetermined pattern is exposed onto a surface of a substrate;
    inspecting the substrate after the lithography by utilizing the method for inspecting the surface as defined in claim 1; and
    performing a lithography in which the pattern is exposed onto a surface of the other substrate.

* * * * *